United States Patent
Hall et al.

(10) Patent No.: US 8,066,681 B1
(45) Date of Patent: Nov. 29, 2011

(54) INTRACRANIAL PRESSURE MONITOR AND DRAINAGE CATHETER ASSEMBLY

(75) Inventors: John P. Hall, Santa Ana, CA (US);
Ronald B. Beckman, Mission Viejo, CA (US)

(73) Assignee: Edwards Life Sciences, Inc., Irvine, CA (US)

( * ) Notice: Subject to any disclaimer, the term of this patent is extended or adjusted under 35 U.S.C. 154(b) by 0 days.

(21) Appl. No.: 08/130,634

(22) Filed: Oct. 1, 1993

Related U.S. Application Data

(63) Continuation of application No. 07/622,250, filed on Dec. 4, 1990, now abandoned, and a continuation-in-part of application No. 07/419,938, filed on Oct. 11, 1989, now abandoned.

(51) Int. Cl.
*A61M 25/00* (2006.01)
*A61M 5/178* (2006.01)
*A61M 39/00* (2006.01)
*A61M 39/10* (2006.01)
*A61M 25/16* (2006.01)
*A61M 25/18* (2006.01)
*A61B 5/00* (2006.01)

(52) U.S. Cl. .............. 604/264; 604/164.01; 604/170.02; 604/533; 600/561

(58) Field of Classification Search .................. 128/667, 128/691, 748, 710, 672–675, 671; 604/164–170, 604/264, 266, 268, 95, 280–282, 170.02, 604/533, 8–10; 600/561
See application file for complete search history.

(56) References Cited

U.S. PATENT DOCUMENTS
2,118,637 A * 8/1938 Wappler
(Continued)

FOREIGN PATENT DOCUMENTS
DE 3127882 2/1983
(Continued)

OTHER PUBLICATIONS

Heart & Lung—The Journal of Critical Care—"Evaluation of New Technology in Critical Care", Hellingsworth Fridlund et al: Mar. 1988, v.17. No. 2.

*Primary Examiner* — Tatyana Zalukaeva
*Assistant Examiner* — Susan Su
(74) *Attorney, Agent, or Firm* — Robert D. Buyan; Stout, Uxa, Buyan & Mullins

(57) ABSTRACT

A monitor-driven intracranial catheter assembly including dual lumen catheter for monitoring intracranial pressure via a pressure sensor located in one lumen while simultaneously draining cerebrospinal fluid through another lumen. A third lumen can also be provided with a side port for receiving a stylet. The stylet is used as a stiffening agent to aid in advancing the catheter into the patient's brain. The pressure sensor is preferably a spectral modulation sensor that communicates with a photodetector apparatus by means of a single optical fiber, thus minimizing the diameter of the catheter. The photodetector is self-correcting for signal errors caused by temperature change, changes in intensity of the input light, and transmission losses within the optical apparatus. Moreover, the photodetector operates off the output voltage of the standard hospital monitor by "scaling" the signal from the monitor to provide a pressure measurement signal that emulates the output of a piezoresistive strain gauge sensor or Wheatstone bridge. Therefore, the entire catheter assembly is designed to be used with any of the common types of hospital monitors. The pressure monitoring catheter assembly can be used in any situation requiring very sensitive pressure measurements and can be zeroed and calibrated in situ.

14 Claims, 10 Drawing Sheets

U.S. PATENT DOCUMENTS

| | | | |
|---|---|---|---|
| 2,458,305 A * | 1/1949 | Sanders | 604/287 |
| 2,603,210 A | 7/1952 | Millet | |
| 3,225,762 A | 12/1965 | Guttman | |
| 3,353,410 A | 11/1967 | MacNeil | |
| 3,421,510 A * | 1/1969 | Kettenbach | 604/268 |
| 3,503,116 A | 3/1970 | Strack | |
| 3,714,829 A | 2/1973 | Gilbert | |
| 4,168,703 A * | 9/1979 | Kenigsberg | 128/748 |
| 4,329,058 A | 5/1982 | James et al. | |
| 4,351,342 A * | 9/1982 | Wiita et al. | 601/266 |
| 4,423,725 A * | 1/1984 | Baran et al. | 604/101 |
| 4,446,715 A | 5/1984 | Bailey | |
| 4,578,057 A * | 3/1986 | Sussman | 604/9 |
| 4,578,061 A | 3/1986 | Lemelson | |
| 4,588,395 A | 5/1986 | Lemelson | |
| 4,611,600 A | 9/1986 | Cohen | |
| 4,632,668 A * | 12/1986 | Wilson, Jr. et al. | 604/8 |
| 4,658,829 A | 4/1987 | Wallace | |
| 4,672,974 A | 6/1987 | Lee | |
| 4,678,904 A | 7/1987 | Saaski et al. | |
| 4,682,500 A | 7/1987 | Uda | |
| 4,703,174 A | 10/1987 | Anderson et al. | |
| 4,703,757 A | 11/1987 | Cohen | |
| 4,705,047 A | 11/1987 | Bailey | |
| 4,705,499 A | 11/1987 | Hooven | |
| 4,711,246 A | 12/1987 | Alderson | |
| 4,712,566 A | 12/1987 | Hök | |
| 4,713,049 A * | 12/1987 | Carter | 604/8 |
| 4,722,348 A | 2/1988 | Ligtenberg et al. | |
| 4,723,556 A | 2/1988 | Sussman | |
| 4,730,622 A | 3/1988 | Cohen | |
| 4,735,212 A | 4/1988 | Cohen | |
| 4,737,142 A * | 4/1988 | Heckele | 604/95 |
| 4,738,267 A | 4/1988 | Lozorthes et al. | |
| 4,739,771 A | 4/1988 | Manwaring | |
| 4,787,396 A | 11/1988 | Pidorenki | |
| 4,796,641 A | 1/1989 | Mills et al. | |
| 4,799,474 A * | 1/1989 | Ueda | 604/281 |
| 4,800,749 A | 1/1989 | Merrick | |
| 4,803,992 A | 2/1989 | Lemelson | |
| 4,815,471 A | 3/1989 | Stobie | |
| 4,815,472 A | 3/1989 | Wise et al. | |
| 4,873,986 A * | 10/1989 | Wallace | 128/678 |
| 4,950,232 A * | 8/1990 | Ruzicka et al. | |
| 5,046,497 A * | 9/1991 | Millar | 128/678 |
| 5,078,688 A * | 1/1992 | Lobodzinski et al. | 604/164 |
| 5,117,836 A * | 6/1992 | Millar | 128/748 |
| 5,191,898 A * | 3/1993 | Millar | 128/748 |
| 5,197,457 A * | 3/1993 | Adair | 604/282 |
| 5,242,389 A * | 9/1993 | Schrader et al. | 604/283 |
| 5,312,357 A * | 5/1994 | Buijs et al. | 604/164 |
| 6,210,346 B1 * | 4/2001 | Hall et al. | |

FOREIGN PATENT DOCUMENTS

| | | |
|---|---|---|
| EP | 0127476 | 5/1984 |
| EP | 0251512 | 1/1988 |
| FR | 2378494 | 8/1978 |
| GB | 2205244 | 12/1988 |
| WO | 8503855 | 9/1985 |

* cited by examiner

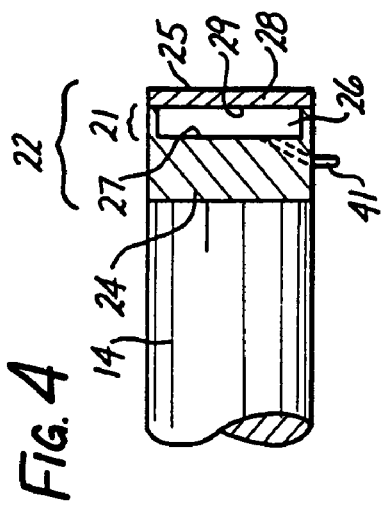
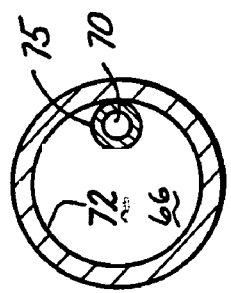
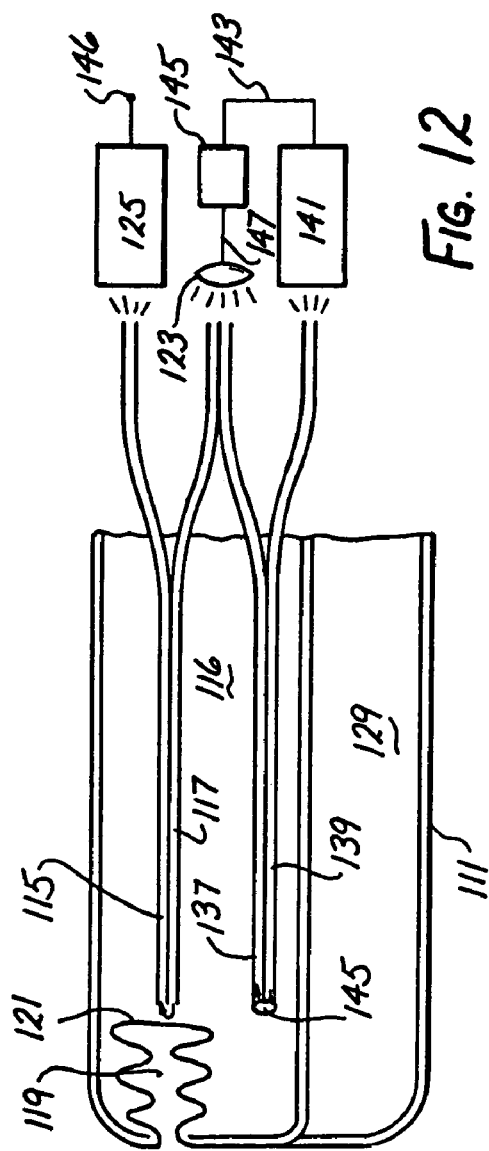

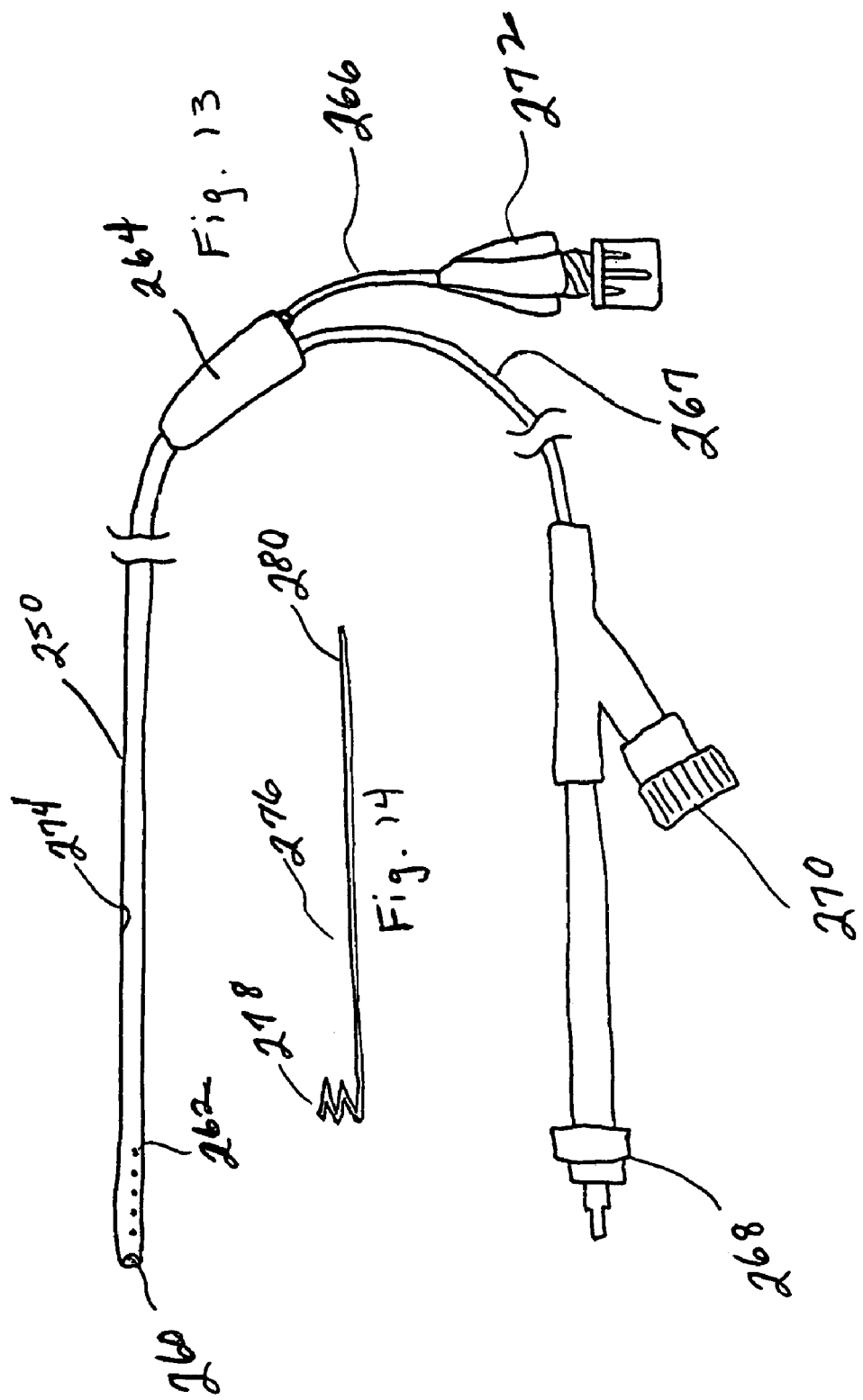

INTRACRANIAL PRESSURE MONITOR AND DRAINAGE CATHETER ASSEMBLY

This is a continuation-in-part of U.S. patent application Ser. No. 419,938 filed Oct. 11, 1989 now abandoned.

BACKGROUND OF THE INVENTION

1. Field of the Invention

The present invention relates to an intracranial catheter that is insertable by a scalp tunnel insertion technique and a related catheter assembly for monitoring fluid pressure while simultaneously removing a part of the fluid or infusing thereinto a second fluid. More particularly, the invention relates to a monitor-driven intracranial catheter assembly including a dual lumen catheter having an in situ pressure monitoring device at the distal tip for continuously monitoring intracranial pressure via one lumen while optionally conducting simultaneous drainage or sampling of cerebrospinal fluid through the other lumen.

2. Description of the Prior Art

The skull is a bony housing of fixed volume containing three types of matter—blood, brain and cerebrospinal fluid—each of which occupies a portion of that volume. If the portion of the volume of one of the three increases without a concomitant fall in the portions of the other two, the intracranial pressure increases. Because the brain has a limited capacity to adapt to increases in intracranial volume, once the limit has been met, small increases in volume cause significant increases in intracranial pressure.

Maintaining cerebral blood flow to provide adequate oxygen and glucose to the brain is critical. However, an increase in the volume of the brain or of cerebral spinal fluid as the result of trauma, and the like, correspondingly constricts the flow of blood and can stop it completely if the increase in fluid is large enough to herniate the brain at the base of the skull. In such cases, death results.

Because it is not practical to monitor cerebral blood flow at the bedside, an algorithm based upon the relationship between mean arterial pressure, intracranial pressure and the cerebral perfusion pressure is used to calculate blood flow in the brain (CPP=MAP−ICP). Thus, a satisfactory means for monitoring intracranial pressure by placement of a pressure transducer into the intraventricular, subarachnoid or intraparentchymal spaces is of utmost importance to the management of head injury cases and has long been sought.

Assemblies for monitoring pressure at various locations within the body are known. The earliest pressure monitoring devices utilize a pressure sensitive diaphragm in contact with a column of sterile fluid contained within a catheter inserted into the blood vessel, the brain, or other area containing a fluid pressure of interest.

Pressure exerted by the fluid, for instance the cerebrospinal or cephalorachitic liquid, is transmitted through the fluid column within the catheter to an external pressure transducer that transforms the pressure signal into an analog or digital form suitable for readout on a monitoring device, such as that commonly used to monitor blood pressure. However, pressure monitoring devices that utilize a column of fluid are easily contaminated with bacteria or air bubbles. Air bubbles in the line distort the pressure readings and bacterial contamination of the fluid may inadvertently expose the patient to sepsis.

The fluid coupled systems used to monitor intracranial pressure access the compartments of the brain by means of a ventricular catheter or bolts placed through the skull. Since the pressures to be monitored are relatively low (0-50 mm Hg), the hydrostatic effects of the fluid column can compromise the readings. Additionally, the fluid column can affect the frequency response of the system.

To eliminate the risks and disadvantages inherent in catheters employing a fluid column for transmitting the pressure reading, improved pressure monitoring devices have been developed that couple the pressure sensitive diaphragm located at the distal end of the catheter with an electrical or optical means for generating a pressure signal and transmitting it to the proximal end of the catheter, and thence to the pressure transducer and monitor. The electrical pressure monitoring diaphragms are typically fitted with a miniaturized Wheatstone bridge strain gauge comprising a series of resistors whose resistance is modified in proportion to the distance from the zero position the diaphragm of the pressure sensor is displaced by the applied pressure. Electrical pressure sensors are commonly employed in hospitals for continuous monitoring of blood pressure and the like. For this reason, hospitals employ monitors adapted to receiving an electrical output from the Wheatstone bridge pressure sensor and transforming it into a pressure reading using well known technology. Thus, an intracranial pressure monitoring catheter employing an electrical pressure sensor could be plugged directly into the pressure monitor found in most hospital rooms without the need for an expensive intervening transducer to modify the signal into a format compatible with the monitor.

However, in designing a pressure monitoring assembly for monitoring intracranial pressure, special considerations are required. Inherent in all electrical pressure monitoring sensors is a risk of electrical shock that may render them unsuitable for insertion into the interior of the brain. Introducing electrical currents into the brain risks permanent damage.

Optical pressure monitoring transducers avoid this risk. Optical pressure sensors generally employ a light reflective diaphragm placed at the distal tip of an optical fiber. Displacement of the reflective diaphragm by applied pressure changes the intensity and/or other spectral characteristics of the reflected light signal, depending upon the type of reflective sensor used. For instance, European Patent Application 0 127 476 owned by Camino Laboratories, Inc., which is hereby incorporated by reference in its entirety, discloses an optical pressure catheter having a set of optical fibers for transmitting a light beam to and from a transducer which modulates the intensity of the reflected light in accordance with the sensed pressure. A photosensor comprising a bellows compressible by pressure is located at the distal end of the catheter and a photodetector located at the proximal end of the catheter measures the modulated intensity of the returned beam and produces a corresponding measurement signal. However, optical transducers operating upon the principles of intensity modulation suffer from the drawback that any curvature of the fiber optic extraneously reduces the intensity of the reflected light.

To overcome this source of error the Camino catheter preferably also contains a second set of optical fibers for transmitting a reference light beam to and from the location of the sensor. The reference light beam is sent to a second photosensor that measures the intensity of the returned reference light beam and produces a correction signal that compensates for variations in transmittance caused by bending of the catheter.

One of the disadvantages of the Camino system for monitoring intracranial pressure is that a dedicated stand alone interface module, such as that manufactured by Camino Laboratories, is required to display the pressure and communicate with various commercial patient monitors. Zeroing is also dependent upon the interface module, which "reads" the characteristics of the individual sensor and provides for zeroing by means of a screw type adjustment. Additionally, to reduce the error caused by bending the optical fibers, intracranial pressure catheters that rely upon modulated intensity of the reflected beam must be very rigid in construction and are therefore inserted into the skull via a bolt. The most reliable intensity modulation catheters, since they require four optical fibers, are larger, more invasive, and therefore inherently more dangerous, than is desirable.

Optical pressure transducers that modulate the wavelength of the reflected light in accordance with the variable to be measured are also known. For instance, U.S. Pat. Nos. 4,329,058 and 4,678,904, which are hereby incorporated by reference in their entirety, describe an optical transducer having an optically resonant sensor by which the wavelength of the reflected light is modified if the reflective diaphragm is deflected by applied pressure from its zero position. This kind of pressure transducer incorporates a Fabry-Perot interferometer in the reflective sensor.

The Fabry-Perot interferometer operates according to well-known principles whereby the gap between two reflective surfaces causes a plurality of reflections and splittings of a single beam of incident light, such that constructive and destructive interference of the components of the incident light beam may occur numerous times. Inasmuch as an inherent phase reversal occurs when light is reflected from a more dense medium to a less dense medium (for example, when it passes through the diaphragm of the optical sensor to the air or other medium in the Fabry-Perot gap), it is possible for the main reflected light beams to cancel in a gap having a width equal to a multiple of half wavelengths of the incident light. Light beams transmitted through the Fabry-Perot gap and the surface of the sensor (those not having half wavelengths in multiples of the gap width) undergo an even number of reflections, so that, in the event of the phase reversal above described, the even number of phase reversals produces no net phase reversal. These light beams transmitted through the gap are in constructive interference with each other and are therefore transmitted through the gap and returned to the photosensor assembly for processing. Under conditions of high reflectivity, even a small variation in the frequency of light caused by passage through the Fabry-Perot interferometer dramatically reduces transmission of the frequency-altered light beams.

Based upon these principles (See Handbook of Physics, 2d, published by McGraw-Hill Section 7, Chapter 5, Part 6 for further information), a Fabry-Perot sensor having a displaceable diaphragm can be used to monitor a physical variable such as applied pressure, temperature, gas density or pH value. In operation, the gap width varies as a function of the physical parameter to be measured. Therefore, the width in the gap corresponding to an applied pressure can be used to measure the pressure. As is described in full detail in U.S. Pat. No. 4,908,474, photodetector circuits can readily compare the incident and reflected light beams to determine the width of the Fabry-Perot gap and compute the magnitude of the sensed variable therefrom. For example, the Model 1400 multisensor system manufactured by Metricor (Woodenville, Wash.) can be used with a Fabry-Perot sensor to detect pressure readings generated by as little as a single Angstrom of change in the gap width.

The changes in intensity or in wavelength in reflected light beams can be converted to a signal compatible with conventional monitors for display as a digital readout or printout by a suitable pressure transducer. However, known pressure transducers having this capability, such as those useful for monitoring intracranial pressure arg expensive and cumbersome. For instance, U.S. Pat. Nos. 4,611,600, 4,703,174, and 4,705,047 disclose various types of transducer circuits suitable for receiving reflected light beams and processing them to yield signals to the monitor that indicate the value of the parameter of interest. However, there is great need for an inexpensive optical pressure transducer, preferably one employing modern techniques of microcircuitry, that operates off the output voltage of the common hospital pressure monitor and produces a modified electrical signal (such as that supplied by the output from a Wheatstone bridge electrical strain gauge) suitable for input to the same bedside monitor.

Intracranial pressure monitoring devices are needed to monitor dangerously high intracranial pressures. One means of reducing elevated intracranial pressure is to drain off cerebrospinal fluid. Thus, a need exists, not only for intracranial pressure monitors, but also for devices for draining fluid from the brain, without inflicting unnecessary damage.

The pressure monitoring device must be inserted into the interior of the skull through a drillhole. If a second hole is drilled to insert a drain, the risk of trauma is obviously doubled. Thus, the need exists for a single device capable of simultaneously monitoring intracranial pressure and draining cerebrospinal fluid.

Simultaneous optical pressure monitoring and drainage assemblies are known. For instance, the Camino intensity modulation sensor can be used with an auxiliary drain inserted into the skull through a bolt. However, the assembly is subject to breakage, requires a large drillhole to accommodate the bolt, and is assembled out of standard connectors that are subject to leakage and, therefore, provide sources of infection. However, an optical pressure monitoring and drainage assembly is highly desirable because the accuracy of fluid column intracranial sensors is destroyed by simultaneous drainage of cerebrospinal fluids. What is needed is an integral fiber optic pressure transducer and simultaneous drainage system that interfaces with conventional monitors via a low cost processor.

All pressure monitoring systems require calibration. In pressure monitoring systems utilizing two fluid reservoirs separated by a diaphragm, such as the fluid column pressure sensor, one reservoir is usually in pressure communication with the local atmosphere, while the other, the applied pressure, is connected to the pressure source to be measured. If the atmospheric pressure is also placed momentarily on the applied pressure input, then the diaphragm moves to the zero point location, and the zero pressure offset error can be measured. However, an implanted catheter, such as an intracranial catheter, cannot be removed for calibration and replaced without introducing the risk of infection. Thus, calibration must be accomplished in situ within the brain.

One means of calibrating a pressure sensor is to provide a substitute pressure transducer system for generating a known test pressure that is displayed on the monitoring device as a calibrated output indicating the level of the known pressure. Another method is that employed by the Model CT/6FB catheter tip pressure transducer manufactured by Medical Measurements Incorporated. In this system the sensor, which includes a mechanical stop to indicate the zero pressure location of the transducer, is depressurized in vivo and calibrated using a micromanometer to provide known test pressures. Thus the zero pressure error and calibration error can be determined. For pressure sensors used in monitoring intracranial pressure, it is particularly desirable to calibrate the sensor in situ so that the sensor can be left in place for up to five days, thereby minimizing the risks of infection and the like. Therefore, the need exists for new and improved pressure monitoring systems such as a dual lumen catheter for monitoring fluid pressure via a first lumen while simultaneously withdrawing an amount of the fluid being measured or infusing a second fluid through a second lumen. And for monitoring intracranial pressure, what is particularly needed is an integrated intracranial pressure monitor and drain assembly, preferably one employing a Fabry-Perot sensor and providing an output signal to standard hospital monitors that "looks like" the signal generated by Wheatstone bridge strain gauge sensors.

SUMMARY

The catheter of this invention is used in a pressure monitoring assembly that comprises, in basic form, a catheter housing having at least one lumen containing a pressure sensor means for generating a pressure signal, which sensor is in communication with a transducer means for converting the output pressure signal from the sensor into electrical signals. Optionally, the sensor has a vent to provide fluid communication with a reference pressure via the first lumen. The catheter usually contains a second lumen that serves as a fluid conduit for infusing or draining fluids through the catheter while monitoring pressure. In addition, the second lumen is adapted to receive a stylet, which is inserted therein as a stiffening agent while the catheter is placed into the brain or other location of operation.

In a preferred embodiment of the present invention, the catheter is a multiple lumen catheter having at least three lumens, the pressure sensing lumen, the drainage lumen and a lumen for insertion of a stylet. Preferably, the stylet lumen has a side port located between the distal end and the proximal end of the catheter to receive the stylet. The stylet lumen is closed at the distal end. Thus, a stylet can be inserted into the side port and fed through the lumen toward the distal tip of the catheter and used as a stiffening agent while the catheter is being advanced into the patient's brain.

In another preferred embodiment of the present invention, the catheter has six lumens, a pressure sensing lumen, three drainage lumens, a stylet lumen with the side port for insertion of the stylet and a lumen for a tensile member or stiffener.

Preferably, the above-described catheter is an integral intracranial pressure monitoring and drainage catheter used in a pressure monitoring assembly that comprises, in basic form, a light source, one or more light transmission means, one or more spectral modulation sensors having optically resonant structures, a photodetector means for converting the output light from the spectral modulation sensor(s) into electrical signals of the type generated by a Wheatstone bridge piezoresistive strain gauge, and a monitor means for receiving the signals and displaying the pressure measurement(s). The catheter allows for simultaneous intracranial pressure monitoring and drainage of cerebrospinal fluids.

Further in accordance with the invention, there is provided an intracranial catheter that is insertable into the skull, through a bore hole formed in the skull, using a scalp-tunnel insertion technique. The catheter is flexible and has a proximal end and a distal end. A stylet lumen is formed within the catheter and is closed at its distal end. A side port is formed in the catheter at a location between its proximal and distal ends (e.g., approximately 4 inches from the distal end of the catheter), in communication with the stylet lumen. A stylet is insertable through the side port and advanceable through the stylet lumen, in the distal direction, until it contacts the closed distal end of the stylet lumen. In this manner, the stylet stiffens only that portion of the catheter that extends distal of the side port.

It is a feature of the preferred embodiment that the monitor provides the excitation voltage to the photodetector and that the photodetector scales the excitation voltage to create the measurement signal(s), which are returned to the monitor to be displayed as the pressure measurement(s).

BRIEF DESCRIPTION OF THE FIGURES

FIG. 2 is a cross-sectional view of another embodiment of the catheter of the present invention.

FIG. 4 is an illustration of a spectral modulation sensor.

FIG. 12 is an illustration with partial cut-away view of the catheter assembly employing an intensity modulation sensor.

FIG. 13 is an illustration of a second preferred embodiment of the catheter of the present invention having six lumens, including a stylet lumen.

FIG. 14 is an illustration of a stylet for use with the catheter shown in FIG. 13.

DESCRIPTION OF THE PREFERRED EMBODIMENT

Figure 1:
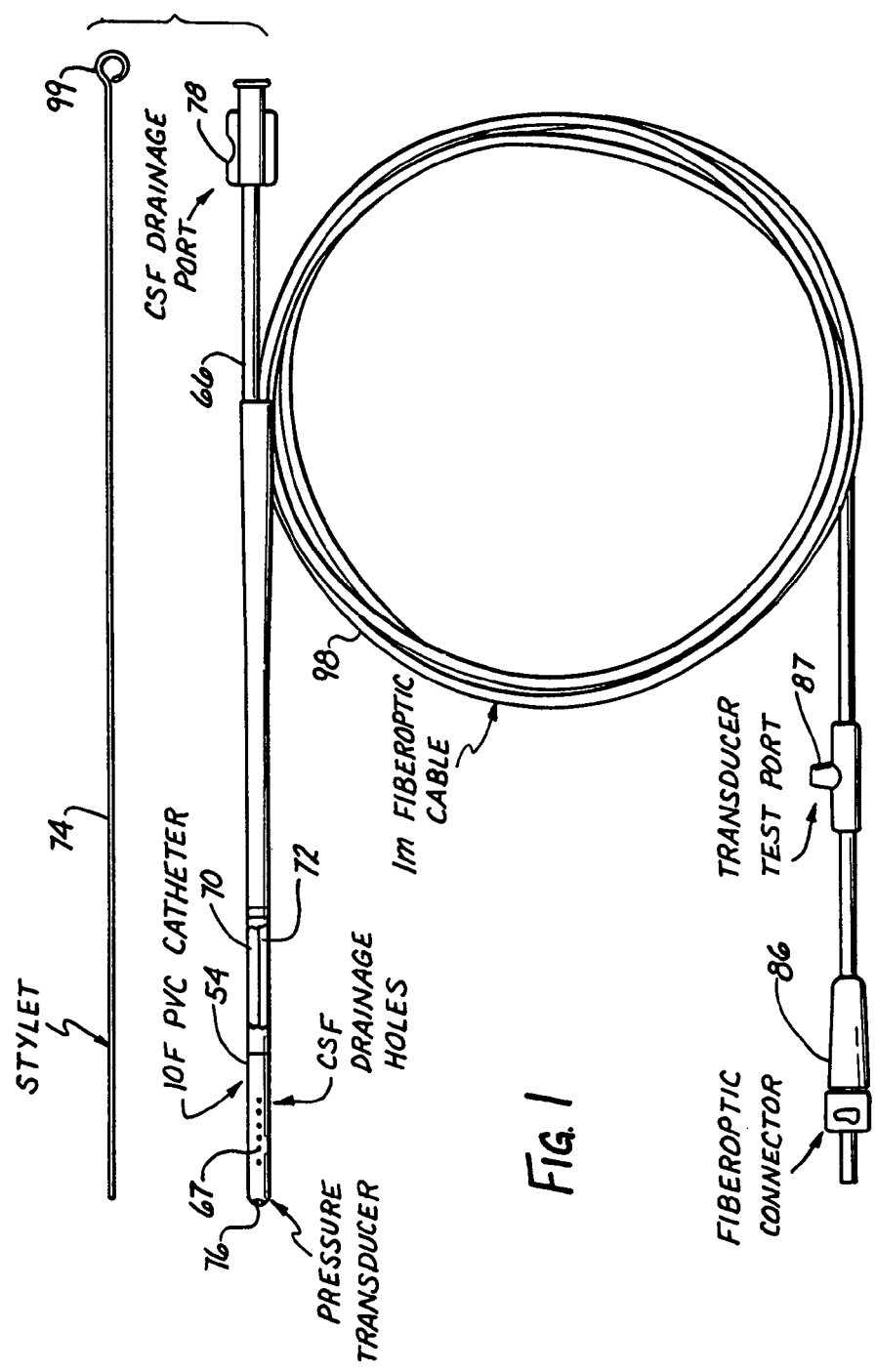
FIG. 1 is an illustration, partially in section, of the preferred embodiment of the catheter and stylet of the present invention.

In the preferred embodiment, the catheter is a dual lumen catheter adapted for insertion into the ventricular and/or parenchymal spaces of the brain of humans and other mammals for measuring intracranial pressure and for simultaneously draining cerebrospinal fluids. As shown in FIG. 1, the catheter comprises catheter housing 54, which encloses first lumen 70 and optional second lumen 72.

Catheter housing 54 is an elongate flexible tube closed at the distal end, except for sensor aperture 76, to facilitate insertion of the catheter into the environment whose pressure is to be monitored. Sensor aperture 76 opens into the distal end of first lumen 70 and provides external fluid access to the pressure sensor.

Usually catheter housing 54 is extruded from a biocompatible plastic material, preferably silicone rubber. Catheter housing 54 is elongate, flexible and sized to be passed through a borehole in the skull and received within the brain.

First lumen 70 extends continuously from the proximal end to sensor aperture 76 at the distal tip of the catheter housing and has a diameter of between about 0.005 and 0.050 inch for containing a pressure sensor and a means for transmitting to the proximal end of catheter housing 54 a signal containing information regarding the pressure measurement sensed by the sensor.

The pressure sensor can be any known pressure sensor device suitable for insertion into a catheter. However, catheters are primarily useful for operations that require the least intrusive means of measuring pressure. Therefore, the pressure sensor is usually selected to minimize the diameter of first lumen 70.

Non-limiting examples of the types of pressure sensors that can be housed within the first lumen fall into four types. The first are fluid column sensors wherein the pressure measurement is transmitted from the distal to the proximal end of the catheter housing via a column of fluid. Usually, a transducer located externally to the catheter housing generates an electrical signal from the measurement signal provided by the fluid column. A second type of sensor employs piezo-resistive strain gauge pressure sensors wherein the change in resistance of small resistors located in the sensor upon a pressure sensitive diaphragm at the distal end of the catheter generates the pressure measurement signal. The electrical pressure measurement signal is transmitted via electrical wires located within the first lumen to a transducer located at the proximal end thereof, usually completely externally to the catheter housing. A third type of pressure sensor employs optical means for generating the pressure measurement signal at the distal end of the catheter housing and for transmitting the signal to the proximal end thereof. Optical pressure sensors usually transmit the pressure signal by means of at least one optical fiber located within the first lumen of the catheter housing.

There are two known basic types of optical pressure transducers, those that generate a pressure signal by detecting the degree to which the intensity of a source light beam is modulated when it is reflected from a movable pressure sensitive diaphragm, and those that generate a pressure signal by detecting the constructive and destructive interference in a source light beam when it is reflected from a movable pressure sensitive diaphragm. The latter type of sensor, which employs an optically resonant structure, is preferred herein because such sensors can be made to yield a pressure signal that is linear with pressure over the desired pressure range and because such sensors require a single optical fiber, yet yield measurements of high accuracy.

When an optical pressure sensor is housed within the first lumen, as shown in FIG. 1, the sensor transmits the optical measurement signal via an optical fiber means extending from the first lumen and having located thereon a test port 97 and an optical fiber connector 96 for providing optical communication to a photodetector means (not shown) with which it is in optical communication.

As shown in FIG. 1, catheter housing 54 optionally contains a second lumen 72 for transporting fluids between the distal and proximal ends of catheter housing 54. Second lumen 72 can have any cross-sectional area appropriate to the application for which it is intended. When used as a drain for draining cerebrospinal fluid, for example, lumen 72 has a diameter of between about 0.025 and 0.100 inch and extends continuously from the proximal to the distal end of the catheter housing, opening at the distal end exterior to catheter housing 54 through aperture 68. At the proximal end optional lumen 72 is fluid tightly attached to drain conduit 66 by any suitable means of attachment 78, preferably one containing a drainage port such as a luer lock fitting. Drain conduit 66 can be provided by any flexible tubing material, such as common hospital polyvinlychroride tubing.

Preferably, catheter housing 54 is about six inches in length, and a plurality of apertures 68 opening into second lumen 72 are spaced along the distal end, preferably along about the extreme half inch of the catheter housing. Most preferably, apertures 68 are bore holes having a diameter of from about 0.005 to 0.050 inch, and the bore holes are arranged in three rows along the length of the catheter housing 54, most preferably at 0.100 inch intervals for allowing an unobstructed flow of cerebrospinal or other fluid therethrough.

Optionally, first lumen 70 is in fluid communication with the sensor contained in first lumen 70 via vent 62 (shown in FIGS. 10 and 11) and is used to vent the sensor to the atmosphere or to apply a reference pressure, such as atmospheric pressure, to the sensor for in situ calibration, as is explained in full hereinafter.

In addition, second lumen 72 is optionally adapted to receive therein stylet 74, which is a slim, stiff rod made of any non-brittle material, such as plastic or metal, and has a handle means, such as a loop 99, at one end for inserting and removing the stylet. When inserted into second lumen 72, stylet 74 provides stiffness to the catheter housing while it is being inserted into the brain and can be removed thereafter so that second lumen 72 can be used as a fluid conduit.

In one embodiment shown in FIG. 2 in cross section, first lumen 70 and second lumen 72 have the general arrangement of a tube within a tube. The first lumen is adapted for housing one or more fiber optics and is comprised of a tube 75 having a relatively smaller diameter, for example 0.016 inch, than the diameter of the housing 54, which is, for example 0.170 inch. As is also shown in FIG. 2, first lumen 70 is fixedly attached along one interior side of the larger second lumen 72 such that the remaining open space within the housing forms a second irregularly shaped conduit 66, the exterior of the first lumen having a single cross-sectional point of tangency with the interior circumference of second lumen 72. The catheter housing containing the first and second lumens can optionally be coextruded from silicone rubber. In this embodiment of the invention, apertures 68 are preferably arranged in rows, preferably three rows along the length of second lumen 72, which itself forms the catheter housing, and are preferably located at angles of 90, 180 and 360 degrees around the cross-sectional circumference of second lumen 72 as measured from said point of tangency. When conduit 66 is used for draining or infusing fluids, it is in fluid communication with the exterior of the catheter housing via at least one of apertures 68.

In another embodiment of the catheter of the present invention, at least three lumens are provided, a first lumen for pressure sensing, a second lumen for transporting or draining fluids, and a third lumen for insertion of a stylet used to stiffen the catheter during placement of the catheter into the patient's brain.

In this embodiment, the third lumen extends continuously from the proximal end of the catheter to the distal end. The third lumen is closed at the distal tip by a plug or other suitable means and a side port is provided in the outer peripheral wall of the catheter body in communication with the stylet lumen. The side port is provided at a location proximal to the distal end of the catheter so that when the catheter is inserted into the patient's body, the side port is located outside the patient's body just proximal to the insertion site. In other words, the side port should be provided along the catheter body at a point just proximal to the desired insertion depth of the catheter. In the preferred embodiment of the catheter shown in FIG. 13, the side port is located at approximately 4 inches or 15 cm from the distal tip. A stylet can then be inserted into the side port and advanced distally in the lumen until it contacts the closed end of the lumen at the distal tip.

Figure 15:
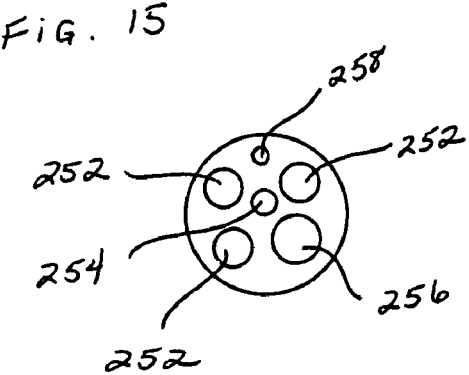
FIG. 15 is a cross-sectional view of the catheter shown in FIG. 13 taken along line 15-15 of FIG. 13.

Referring to FIG. 13, there is shown a preferred embodiment of the catheter of the present invention having six lumens. The catheter housing 250 is an elongate flexible tube extruded from a biocompatible plastic material, preferably silicone rubber. Referring to FIG. 15, the catheter housing has a first lumen 254 for sensing pressure, second, third, and fourth lumens 252 for draining or transporting fluids between the distal and proximal ends of the catheter, a fifth lumen 256 for receiving stylet 276 used to place the distal end of the catheter in the patient's brain, and a sixth lumen 258 containing a tensile (member or stiffener. Each lumen extends continuously from the proximal end to the distal end of the catheter housing 250.

All of the lumens within the catheter housing 250 are closed at the distal end except for the pressure sensing lumen 254 which has an opening or sensor aperture 260 at the distal tip of the catheter housing. Each drainage lumen has a plurality of apertures 262 opening into the lumen and spaced along the distal end of the catheter housing, preferably along the extreme half inch of the catheter housing, as described above in connection with FIG. 1. Accordingly, the catheter housing has three rows of apertures 262 along the length of the catheter, each row opening into a separate drainage lumen 252.

As can clearly be seen from FIGS. 13 and 14, therefore, the catheter of the present invention is useable in the skull area and comprises the catheter body in the form of an elongated rube 250. The lumens in the catheter body, except for the lumen communicating with the pressure sensor opening 260, are closed at the distal end of the tube 250 with, for example, a plug. As described in detail below, a pressure sensor may be positioned at the distal of the tube in communication with the opening 260 and in communication with a connecting part 268 arranged at a rear (i.e., proximal) end of the catheter for connection of the pressure sensor to a pressure monitor. Additionally, the tube 250 has a stylet insertion aperture or opening 274 at a predetermined distance from its distal end. This opening 274 has dimensions that are sufficient to allow insertion of an elongated stylet 276 therethrough and into the tube 250 such that the distal end 280 of the stylet 276 contacts the closed distal end of the catheter tube 250. As is clearly illustrated in FIGS. 16-18, inserting the stylet 276 in this manner facilitates insertion and location of the distal portion of the catheter within the skull while allowing the aperture 274 through which the stylet is inserted to remain exteriorized. The stylet 276 is then removed. Thus, in accordance with the insertion technique shown in FIG. 16 et seq., the distance between the stylet insertion aperture or opening 274 and the closed distal end of the tube 250 is a) greater than the length of tube 250 that has been inserted into the skull and b) less than the length of the stylet 276.

In the preferred embodiment, an optical pressure sensor is housed within the pressure sensing aperture and transmits the optical measurement signal via an optical fiber extending from the sensor through the pressure sensing lumen to the proximal end of the catheter. A connector 264 joins the pressure sensing lumen at the proximal end of the catheter body to optical cable 267. The optical fiber thus extends from the proximal end of the catheter through the optical cable 267 to optical fiber connector 268. Optical fiber connector 268 can then be connected to an instrument containing a photodetector means and means for processing the optical signal to display a pressure reading. A calibration port 270 is provided in cable 267 and communicates with the pressure sensing lumen to provide a reference pressure during pressure monitoring and also serves to apply a calibration pressure for in situ calibration of the pressure sensor.

Drainage conduit 266 is fluid tightly connected to drainage lumen 252 by connector 264 and a drainage port 272 is provided at the proximal end of conduit 266 for attachment to drainage tubing or a fluid reservoir for receiving the fluids.

The stylet lumen or guide lumen 256 is closed at the distal tip by suitable means, such as a silicone plug or the like. A side port or aperture 274 is provided in the catheter housing 254 in communication with the stylet lumen at approximately 4 inches from the distal tip. Thus, stylet 276 shown in FIG. 14 can be inserted into the stylet lumen through side port 274 by holding the handle 278 and advancing the distal end of the stylet 280 toward the distal tip of the catheter housing until the end of the stylet contacts the closed end of the stylet lumen. Stylet 276 is identical to stylet 74 except that it is shorter in length since it is adapted to be used in only the distal portion of the stylet lumen from the side port 274 to the distal tip of the catheter. Whereas stylet 74 is adapted to be inserted through the drainage port 78 shown in FIG. 1 and extends from the proximal end of the drainage lumen to the distal end.

Figure 16:
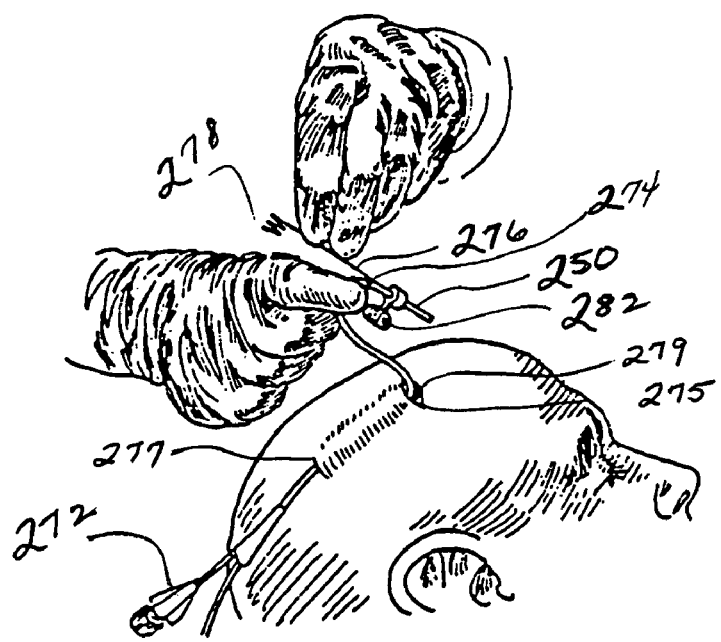
FIG. 16 is a schematic illustration of the insertion of a stylet into the side port of the stylet lumen of the catheter of the present invention.

Stylet 276 and 74 both serve to stiffen the catheter during insertion of the catheter into the patient's brain. Referring to FIG. 16, a schematic drawing illustrates the insertion of the stylet 276 into the side port 274 of the stylet lumen 256 in preparation for advancing the catheter through a bore hole in the patient's skull and through the brain into the ventricle or other area in which the intracranial pressure will be monitored.

To insert the catheter, the neurosurgeon may use the following tunnelling technique. The neurosurgeon first makes two incisions in the scalp, a first incision 275 at the desired location for the bore hole and a second incision 277 several inches away from the bore hole location. Bore hole 279 is then drilled into the patient's skull at the location of the first incision 275. The flap of skin between the two incisions serves as a tunnel between the scalp and the skull through which the distal end of the catheter is fed before advancing it into the bore hole. The tunnel is designed to minimize or prevent bacterial infection at the sterile site of the bore hole. The contaminants and bacteria that may contact the proximal end of the catheter near the drainage connector or optical connector could reach the bore hole by migrating along the catheter body. The tunnel provides a conduit where the body's immune system can attack any bacteria or other contaminants that may migrate along the catheter body and, therefore, prevent them from entering the bore hole and infecting the brain.

Figure 17:
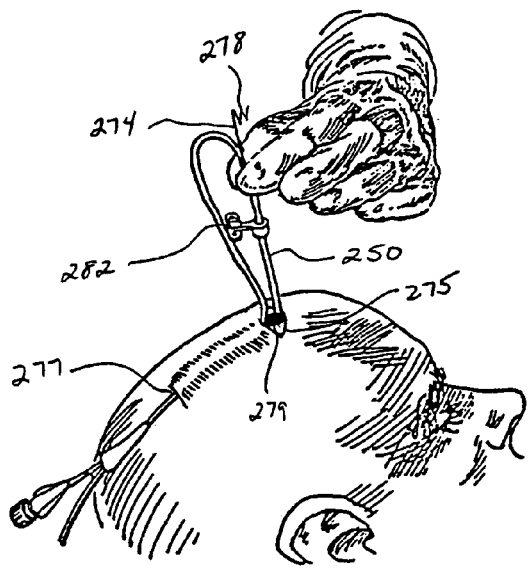
FIG. 17 is a schematic illustration of the advancement of the catheter of the present invention into the ventricle of the brain using a stylet inserted into the side port of the stylet lumen.

After the distal end of the catheter is fed through the tunnel, the physician pulls it up and away from bore hole 279 as shown in FIG. 16 and then inserts stylet 276 into side port 274. The physician then inserts the distal end of the catheter into bore hole 279 and advances the catheter into the patient's brain with the aid of the stylet as shown in FIG. 17.

Figure 18:
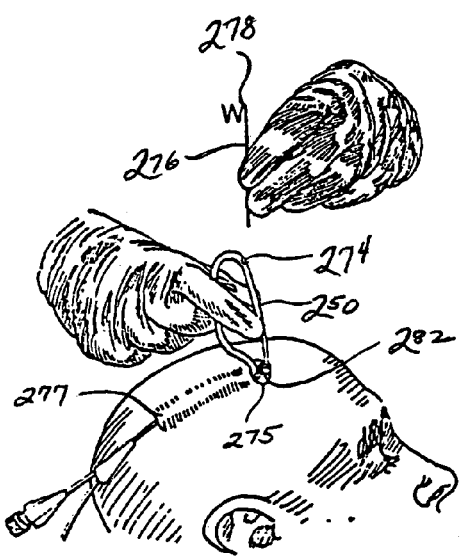
FIG. 18 is a schematic illustration of the removal of the stylet from the side port of the stylet lumen of the catheter of the present invention.

After the catheter has been advanced to the desired location, stylet 276 is removed as shown in FIG. 18. The excess length of the catheter can then be pulled back through the tunnel.

A suture loop 282 is attached to the catheter 250 near the distal end and can be used to suture the catheter in place once the catheter has been advanced into the patient to the desired location.

The preferred pressure sensor housed within first lumen 70 of the catheter shown in FIG. 2 or in lumen 254 of the catheter shown in FIG. 13 is a spectral modulation sensor located at the distal end thereof. The light transmission means comprises an input optical fiber, an optical beam splitter, an optical fiber connector, a sensor optical fiber, and an output optical fiber. The optical beam splitter and optical fiber connector optically connect the sensor optical fiber with the input and output optical fibers.

A single optical fiber namely the sensor optical fiber, acts to both convey input light to the spectral modulation sensor and to convey output light reflected therefrom. This simplifies the optical measuring device, reduces its size and cost, and increases its reliability as compared to a system employing two or more optical fibers for conveying light to and from the sensor. Moreover, the use of a single optical fiber reduces the external diameter of the catheter to a minimum and leaves open space surrounding the optical fiber within the first lumen proximal to the sensor, which open space can be used to vent the sensor to a reference pressure via a vent in the sensor substrate, the first lumen and the vent serving as a conduit to the cavity between the reflective surfaces of the sensor.

The spectral modulation sensor has as its active element an optically resonant structure, comprising a pair of separated reflective surfaces, with the reflectivity and transmission of the resonant structure being a function of the distance between its reflective surfaces. In a spectral modulation sensor, the optical characteristics of its reflecting surfaces, and the index of refraction of the medium between its reflective surfaces will also affect the reflectivity and transmission of the sensor; therefore, in this invention the said medium is held constant so as to have no effect upon the measurement signal.

Thus, if the distance between the reflective surfaces of the spectral modulation sensor's optically resonant structure is altered by the pressure being measured, then the light reflected and/or transmitted by the spectral modulation sensor will change as a function of the measured pressure. Accordingly, the output light from the spectral modulation sensor will be spectrally modulated by its optically resonant structure as a function of the pressure measured and carries information regarding the physical parameter being measured. The spectrally modulated output light from the spectral modulation sensor is converted into an output electrical signal by the photodetector means which comprises photodetector and amplifier means. The output electrical signal provides an accurate determination of the physical parameter being measured, within a certain range of values for the pressure being measured once the optical measuring device has been calibrated.

However, the basic form of the invention may be susceptible to measurement inaccuracies due to two causes. The first cause is changes in the light source intensity or in light transmission intensity due to bending of the optical fibers or due to optical connector light loss. These inaccuracies can be eliminated if the light source is selected to emit light over at least two wavelengths such as is provided by a light emitting diode (LED), for example. A second cause of inaccuracy is spectral modulations in light from light emitting diodes caused by a change in temperature of the diode.

The inaccuracies caused by transmission loss and variations in the light source can be corrected automatically by the detection means if the spectrally modulated output light wavelength(s) from the spectral modulation sensor are separated into two spectral components, each of which is separately converted into an electrical signal by photodetector means and then amplified. The two amplified signals are sent to a divider circuit that takes the ratio of the two electrical signals to provide an output signal that is accurate within a certain range of values for the physical parameter being measured, once the optical measuring device has been calibrated.

Because changes in the light source intensity or in light transmission intensity due to bending of optical fibers normally effect the two spectral components of the spectral modulation sensor equally, when the two electrical signals corresponding to the two spectral components are divided in the divider circuit, such changes cancel each other out and have no effect on the output signal from the divider circuit.

To self-correct for temperature caused inaccuracies in the apparatus, the optical fiber beam splitter contains a filter that separates the spectrally modulated output light wavelengths from the spectral modulation sensor into two spectral components. This filter is selected to incorporate a temperature effect upon the spectrum of light emitted from it that matches or "tracks" the spectral temperature effect of the light emitting diode with which it is in optical communication. By this matching of the spectral shift in the LED with that in the filter, the detection means provides a self-correcting device for removing any spectral modulation in the output light caused by a change in temperature of the diode during operation of the apparatus.

Thus, the invention features a self-correcting detection means requiring no adjustment by the operator during/operation.

Figure 3:
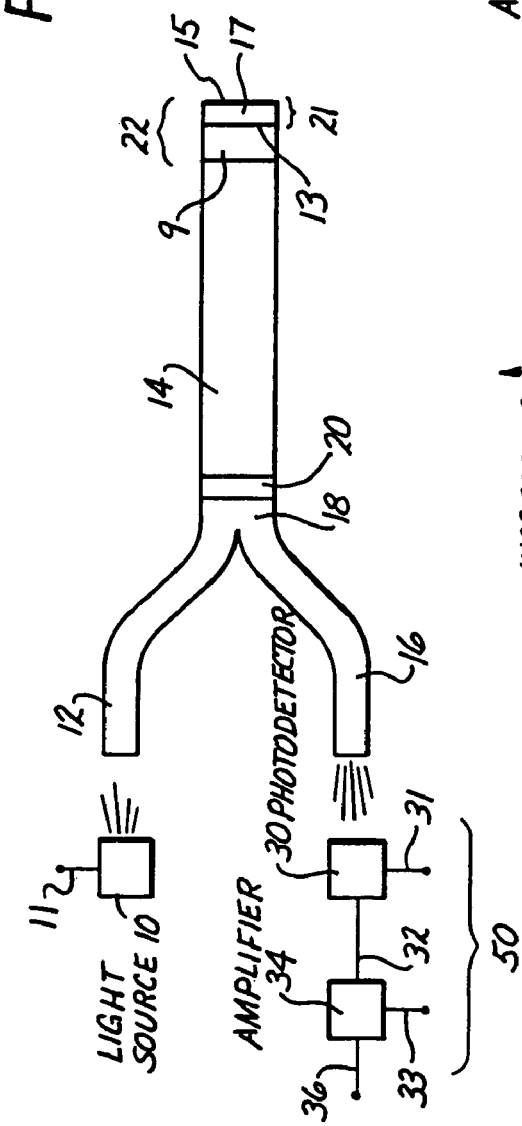
FIG. 3 is a schematic illustration of the catheter assembly employing a spectral modulation sensor.

Tanning now to FIG. 3, the first embodiment of the integral pressure sensor and fluid transport catheter assembly is schematically illustrated. Light source 10 is for providing suitable measuring input light, which may be monochromatic or which may be dispersed over two or more adjacent or nonadjacent wavelengths bands. Light source 10 can comprise a single source of monochromatic light, such as a laser or a lasing diode, a source of two or more wavelengths such as a light emitting diode, and/or suitable optical filters to provide the desired input light. Power for light source 10 is provided by any suitable source of electrical power through conventional electrical connection means 11.

Input light from light source 10 is coupled into sensor optical fiber 14 via input optical fiber 12, optical beam splitter 18 and optical fiber connector 20.

Optically connected to the end of optical sensor fiber 14, and receiving input light therefrom, is a spectral modulation sensor 22 having an optional substrate 9 supporting an optically resonant structure 21. If used, substrate 9 preferably has a thickness about equal to the diameter of sensor optical fiber 14. Improved sensitivity of optically resonant structure 21 results if substrate 9 is used because light entering optically resonant structure 21 from sensor optical fiber 14 is relatively more collimated than if substrate 9 were omitted and sensor 22 were secured directly to the end of sensor optical fiber 14. If substrate 9 is omitted, optically resonant structure 21 is secured directly to the end of sensor optical fiber 14. Substrate 9 serves as an aid in the manufacture of sensor 22 and in the assembly of optically resonant structure 21 to the end of sensor optical fiber 14, since as well known, optically resonant structure 21 can be less than 1 micron thick. Preferably, substrate 9 does not play a part in spectrally modulating the measuring input light to optically resonant structure 21, but it could do so.

Optically resonant structure 21 comprises, in general, a pair of separated reflective surfaces 13 and 15 with the reflectivity and transmission of the optically resonant structure being a function of its optically physical sensitive characteristics, such as the distance between reflective surfaces 13 and 15, the optical characteristics of reflective surfaces 13 and 15, and the index of refraction of any medium located within cavity 17 between reflective surfaces 13 and 15. In this invention, the output light from sensor 22 is spectrally modulated by optically resonant structure 21 as a function of the distance between reflective surfaces 13 and 15. For measuring fluid pressure, it is further preferred that the medium in cavity 17 be either a vacuum or air, both of which have an index of refraction of one and therefore have no effect upon the reflectivity and transmission of the optically resonant structure.

Spectrally modulated output light from sensor 22 travels sequentially through sensor optical fiber 14, optical fiber connector 20, optical beam splitter 18 and output optical fiber 16 where it is optically coupled to photodetector 30 in photodetector assembly 50. Photodetector assembly 50 comprises photodetector 30, and amplifier 34, which receives an output signal from photodetector 30 via electrical connection means 32. The amplified output signal from amplifier 34 is delivered to output terminal 36, and provides a measurement of the sensed pressure.

Power is provided from any suitable source to photodetector 30 and amplifier 34 through electrical connection means 31 and 33, respectively.

Spectral modulation sensor 22 is shown in FIG. 4 in greater detail. Sensor 22 preferably comprises a cylindrical substrate 24 defining a cylindrical cavity 26 and has a cover 28 which covers cavity 26. Cavity 26 has a reflective bottom surface 27 while cover 28 has a reflective inner surface 29 and an outer surface 25, surfaces 27 and 29 being parallel. It is preferred, but not required, that the thickness of substrate 24 between bottom 27 and the end of sensor optical fiber 14 be as was discussed regarding substrate 9 of sensor 22 with regard to FIG. 3.

If an absolute pressure sensor is desired, then cavity 26 is preferably evacuated, cover 28 providing it with a fluidtight seal. Alternatively, if a differential pressure sensor 22 is desired, cavity 26 is in fluid communication via optional conduit 41 and the first lumen (not shown) with a source of pressure, such as atmospheric pressure, while a source of applied pressure bears against outside surface 25 of cover 28. Naturally, optional conduit 41 is omitted if sensor 22 is to be an absolute pressure sensor.

Reflective surfaces 27 and 29 are preferably coated with about 100 to 200 Angstroms of high refractive index transparent media, for reasons explained hereinafter.

Cavity 26, its reflective bottom 27, and reflective innersurface 29 of cover 28 form optically resonant structure 21. As alternative constructions for sensor 22, it is of course possible to form cavity 26 in cover 28 rather than in substrate 24; or even to form cavity 26 partially in substrate 24 and partially in cover 28, without departing from the scope of the invention.

The method of making sensor 22 and its optically resonant structure is described in detail in U.S. Pat. No. 4,678,904, which is incorporated herein by reference in its entirety. It should be noted here, however, that when cavity 26 is evacuated, a getter structure (not shown) in the form of a ring of deposited layers of chrome and iron is optionally deposited in the bottom of each cavity 26 to absorb residual gases or subsequent outgassing in cavity 26 after the initial evacuation thereof is performed. The optional getter structure comprises a donut shaped ring of the deposited chrome and iron layers with an inner diameter of about 140 microns and an outer diameter of about 190 microns centered in bottom 27 of cavity 26. Thus, getter rings leave a clear central portion of about 140 microns in diameter in the bottom of each cavity 26 through which light can pass. After cover 28 is bonded to cavity 26, the getter ring removes gases from cavity 26.

When in operation as an absolute pressure sensor, sensor 22 is subjected to an external pressure such that cover 28 over evacuated cavity 26 is bowed inwardly toward the reflective bottom 27 of cavity 26 to a greater or lesser degree depending upon the amount of external pressure. As the external pressure on cover 28 increases, such bowing increases; and as the external pressure decreases, the bowing decreases and becomes zero when the external pressure is zero.

Thus, as the external pressure on cover 28 increases and decreases the distance between reflective surfaces 27 and 29 of optically resonant structure 21 alters. Changes in the said distance of as little as one Angstrom in length can be detected by the catheter assembly of this invention.

When sensor 22 is operated as a differential pressure sensor, one source of pressure is fluidly communicated to cavity 26, such as through conduit 41 and the first lumen, while surface 25 of cover 28 is exposed to a second source of pressure. Cover 28 will bow inwardly towards reflective bottom 27 of cavity 26 when pressure on surface 25 of cover 28 exceeds that within cavity 26, the amount of bowing depending upon the pressure differential, and will not bow at all when the pressure differential is zero. However, when the pressure within cavity 26 is greater than that on surface 25 of cover 26, cover 28 will bow outwardly, the amount of bowing again depending on the pressure differential.

Whether sensor 22, is used as an absolute or differential pressure sensor, bowing of cover 28 in response to applied pressure alters the distance between reflective surfaces 27 and 29, which in turn produces corresponding microshifts in the reflectivity curve and operating segment(s) of optically resonant structure 21 as a function of the pressure to which sensor 22 is subjected, as will be described in greater detail hereinafter. As a result, output light from sensor 22 is spectrally modulated as a function of the pressure to which sensor 22 is subjected and carries accurate information regarding such pressure.

Figure 5:
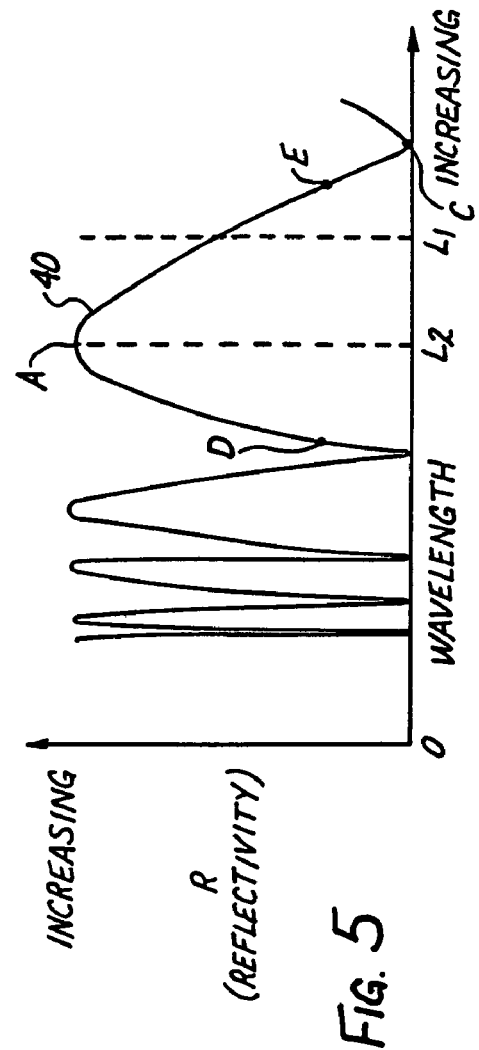
FIG. 5 is a graphic representation of a reflectivity curve for an optically resonant structure.

To make and use sensor 22, a brief summary of its theory of reflectivity is required. The reflectivity R of parallel plane optically resonant structure 21 is well known to be a periodic function of the wavelength of its input light—a common characteristic of optically resonant structures. FIG. 5 shows a typical reflectivity curve 40 of parallel plane optically resonant structure 21 having a given set of physical characteristics. It should be particularly noted that reflectivity curve 40 also represents the reflectivity curve of optically resonant structure 21 when the reflective surfaces are not parallel (i.e., when the moveable diaphragm is not in the zero position). Reflectivity R of parallel plane optically resonant structure 21 is known to be given by the equation:

$$R = 1 - s^2/((1-r)^2 + 4r^2 \sin^2(\theta))$$

Where $s = (s_1, s_2)^{0.5}$ and $r = (r_1, r_2)^{0.5}$

The quantities $s_1, s_2$ are, respectively, the transmittances of reflective surfaces 13 and 15 while $r_1, r_2$ are, respectively, the reflectances of reflected surfaces 13 and 15 (or 27 and 29) as seen from within parallel plane optically resonant structure 21. The angle theta in the sine term of the above equation is known to be given by:

$$\theta = 2(\pi)nt\cos(\phi)/\lambda + e$$

Where:
n=the refractive index of medium 17 between reflective surfaces 13 and 15;
t=the distance between reflective surfaces 13 and 15;
phi=the angle of light reflection between reflective surfaces 13 and 15;
lambda=the wavelength of input light impinging on optically resonant structure 21;
e=any phase shift caused by reflection from either reflective surface 13 or 15.

Parallel plane optically resonant structure 21 is designed so that parameter group nt cos(phi)/lambda changes in response to applied pressure as distance t changes. Thus, for any selected wavelength of input light, parallel plane optically resonant structure 21 will exhibit varying reflectivity as a function of pressure.

Figure 6:
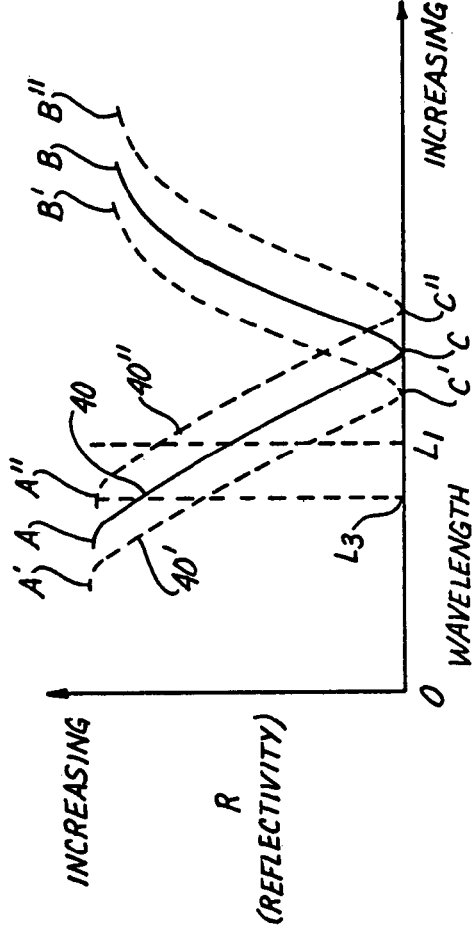
FIG. 6 shows a portion of the curve of FIG. 5 during operation of the spectral modulation sensor.

FIG. 6, which shows an enlarged portion of reflectivity curve 40, illustrates the effect on reflectivity curve 40 when distance t between the reflective surfaces of its particular corresponding optically resonant structure 21 is altered.

As is also seen in FIG. 6, reflectivity curve 40 of optically resonant structure 21 is shifted to the left, with respect to any particular selected wavelength $L_1$ of input light from light source 10, to become reflectivity curve 40' when the distance between its reflective surfaces 13 and 15 is reduced; and it is shifted to the right with respect to $L_1$ to become reflectivity curve 40" when the distance between its reflective surfaces 13 and 15 is increased.

By way of nonlimiting example, a resonance cycle on reflectivity curve 40 of any optically resonant structure 21 is AB, as seen in FIG. 6.

In general the reflectivity curve of any optically resonant structure 21 shifts left and/or right with respect to wavelength $L_1$ as a function of any change in the distance between its reflective surfaces, and hence as a function of any change in the measured pressure, such shifts being termed herein microshifts. The resonant cycle of the reflectivity curve of any optically resonant structure 21 is defined as one complete cycle on its reflectivity curve. There are, of course, a plurality of such resonance cycles on its reflectivity curve since a resonance cycle may start anywhere on its reflectivity curve.

It is known that accurate measurements of pressure can be made using operating segments of the reflectivity curve of the particular optical resonant structure 21 that are less than about one resonant cycle in length and by using operating segment microshifts which are also less than about one resonance cycle in length at the measuring input light wavelength(s). As the reflectivity curve is cyclic, there are a plurality of such operating segments on it.

By way of nonlimiting example, if the operating segment of reflectivity curve 40 of FIG. 6 were A"B" it is of course, one resonance cycle in length. Further, if in response to sensed pressure, operating segment A"B" were microshifted to the left until point B" intersected wavelength $L_3$, then the microshift of operating segment A"B" would be one resonance cycle in length.

With regard to the embodiment of the invention wherein light source 10 delivers monochromatic input light of a wavelength, such as $L_1$, wavelength $L_1$ does not change in response to sensed pressure. However, from an inspection of FIG. 6 it is seen that for any given intensity of any input light of wavelength $L_1$ to sensor 22, the output intensity at wavelength $L_1$ will be different when distance t is altered in response to sensed pressure, as compared to distance t when sensed pressure is zero. Thus, operating segment AC of optically resonant structure 21 undergoes a microshift to the left and/or right of operating segment AC (to become A'C' and A"C") in response to the pressure being measured.

Thus, sensor 22 is a spectral modulation sensor whose optically resonant structure 21 modulates input light of wavelength $L_1$ as a function of the pressure being measured and produces modulated output light of light wavelength $L_1$ that carries information regarding the pressure being measured. This information is converted by photodetector 30 and amplifier 34, as has been described, into an electrical output measuring signal carrying the same information.

Naturally, the wavelength(s) of input light from light source 10 and the distance between reflective surfaces 13 and 15 of optically resonant structure 21 are selected such that the wavelength(s) of input measuring light fall at least substantially within the desired operating segment of its reflectivity curve, such as AC for example, over the desired operating range of values for pressure being measured. Thus, as seen in FIG. 6, wavelength $L_1$ remained within operating segment AC, despite operating segment AC being microshifted by optically resonant structure 21 in response to sensed pressure to become A'C' and/or A"C".

Preferably, the operating segment, the wavelength(s) and/or amplitude(s) of the input measuring light are selected to obtain an operating segment of greatest length which will yield unambiguous spectrally modulated output light over the range of values of interest for the pressure being measured.

For example, for a monochromatic input light of wavelength $L_1$, changes in the output light of optically resonant structure 21 are maximized when operating segment AC extends, as illustrated in FIG. 6, between any maxima and adjacent minima (or vice versa) on its reflectivity curve 40, and when the pressure being measured alters optically resonant structure 21 such that its operating segment AC intersects the input measuring light wavelength $L_1$, i.e., is microshifted a full half resonance cycle. Most preferably, only the linear portion of the operating segment is used. So that the spectrally modulated output light bears a unique one to one relationship to the pressure being measured over the range of values of interest.

To maximize sensitivity, it is desirable to increase the maximum to minimum reflectivity difference of optically resonant structure 21, such as between AC in FIG. 6. This is done by coating at least one of reflectivity surfaces 13 and 15 with an appropriate thickness, say 100 to 200 Angstroms, for example, of a high refractive index transparent media that increases surface reflectivity, such as rutile, titanium dioxide, cubic zirconia or silicon.

Figure 7:
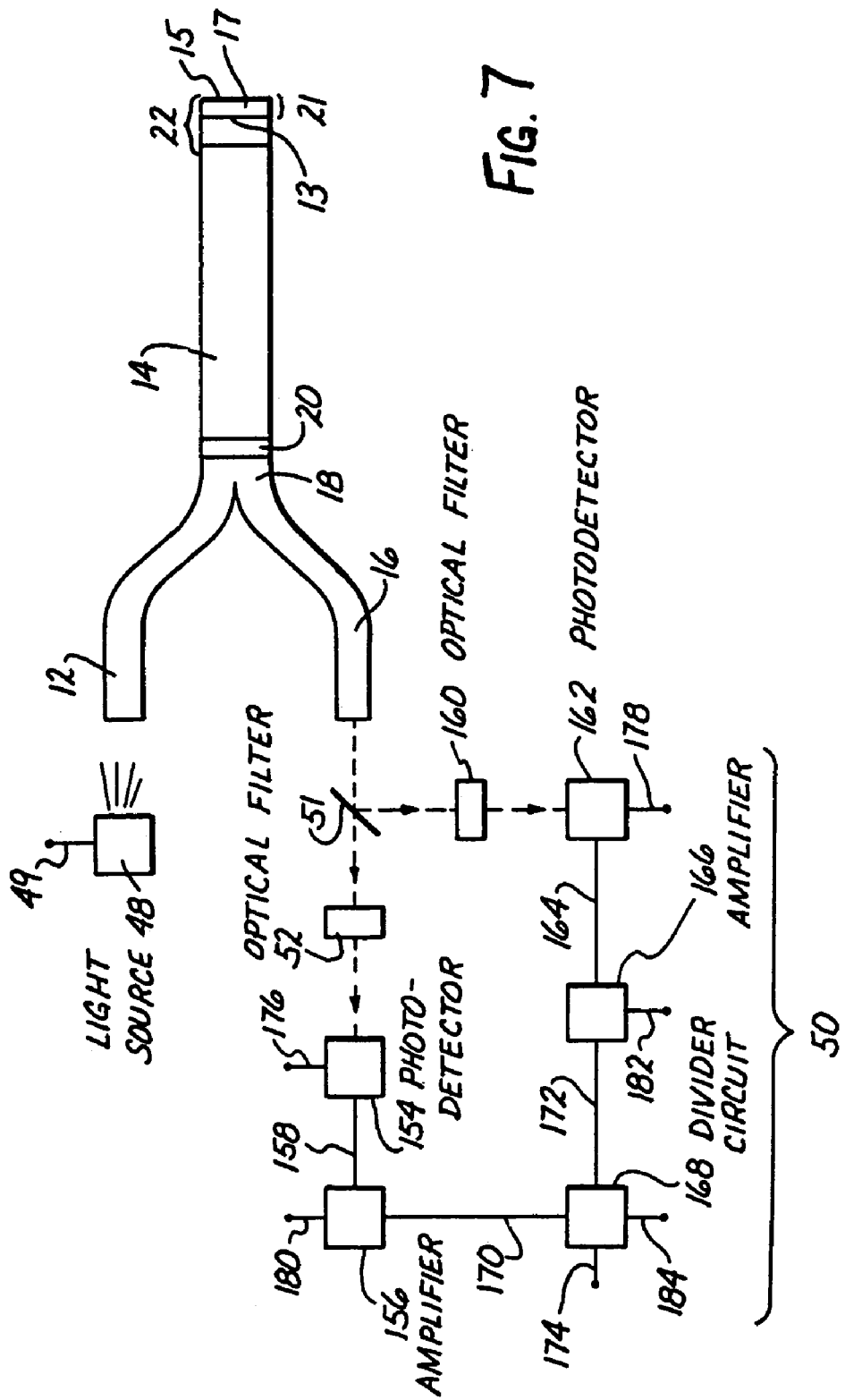
FIG. 7 is a schematic illustration of the catheter assembly employing the spectral modulation sensor with a ratiometric photodetector.

An alternative and preferred embodiment of the invention is illustrated in FIG. 7. In this embodiment, light source 48 is chosen to produce at least two light wavelengths and may be, by way of example, a light emitting diode (LED) which emits a band of light wavelength(s) centered at approximately 810 nm, such as part #MFOE1202, made by the Motorola Company. Power for light source 48 is provided by any suitable source of electrical power through electrical connection means 49.

Spectrally modulated output light from output optical fiber 16 is directed onto a beam splitter 51 which divides it into two output light beams. The first output light beam from beam splitter 51 passes through short pass optical filter 52, which transmit to an appreciable degree only light having a wavelength shorter than a given, preselected wavelength. The short wavelength output light band from filter 52 is converted to a first electrical signal by photodetector 154 and then conveyed to amplifier 156 by electrical connection means 158 to be amplified by amplifier 156. Said preselected wavelengths may be, by way of example, the wavelength of light from light source 48 of highest intensity, such as the wavelength of 810 nm, for the particular LED mentioned above.

The second output light beam from beam splitter 51 passes through long pass optical filter 160, which transmits to an appreciable degree only light having a wavelength longer than said given, preselected wavelength. The long wavelength output light band from filter 160 is converted to a second electrical signal by photodetector 162 and then conveyed by electrical connection means 164 to amplifier 166 to be amplified by amplifier 166. Amplifiers 156,166 preferably amplify their respective signals to the same degree.

The amplified first and second electrical signals from amplifiers 156,166 are conveyed to a divider circuit 168 by electrical connection means 170 and 172. Divider circuit 168 takes a ratio thereof and provides an output measuring signal to electrical connection means 174. The output measuring signal carries information regarding the physical parameter being measured.

Power for photodetectors 154,162, amplifiers 156,166 and divider circuit 168 are provided by any suitable source of electrical power through electrical connections means 176, 178,180,182,184, respectively. Preferably, however, power to the photodetector assembly is provided by a hospital bedside monitor such that the excitation voltage to the photodetector assembly is scaled by amplifiers 156,166 and divider circuit 168 to provide an output signal to the monitor.

In the most preferred embodiment of the invention, the pressure monitoring apparatus employs a multiwavelength light source providing at least two wavelengths of light and a second, reference sensor having a second photodetector for producing a reference signal by operations that repeat the operations described above with reference to the photodetector means depicted in FIG. 7. The photodetector assembly compares the reference signal with the measurement signal to produce an absolute measurement signal that is free from transmission and temperature errors.

Figure 8:
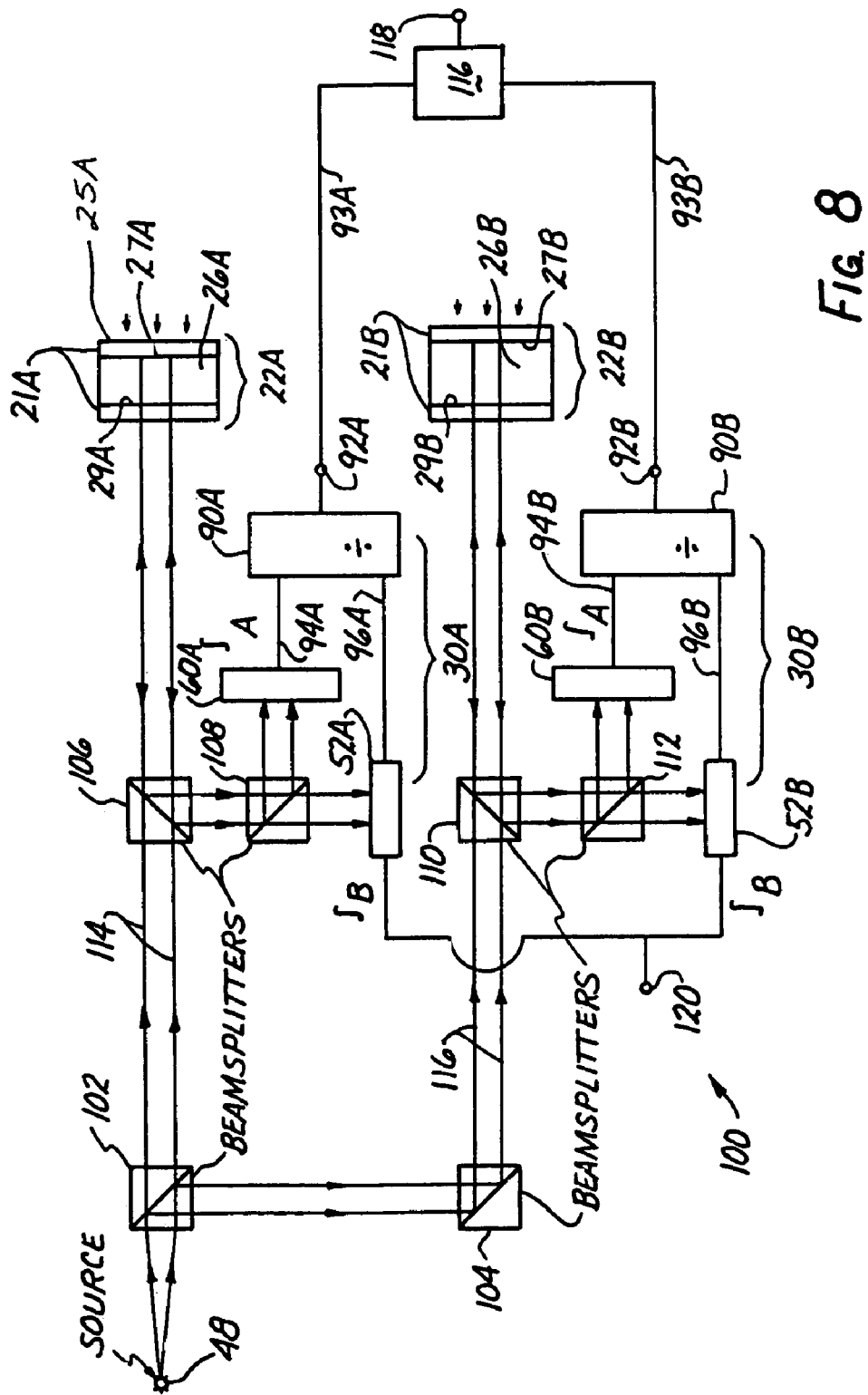
FIG. 8 is a schematic illustration of the catheter assembly employing two spectral modulation sensors with a ratiometric photodetector.

Most preferably, as shown schematically in FIG. 8, the photodetector assembly means 100 splits light received from a single multiwavelength source 48 by means of beamsplitter 102 and steers split beams 114 and 116, each containing at least two light wavelengths, to spectral modulation sensors 22A and 22B by means of optical fibers 16A and 16B (not shown), respectively.

Sensor 22A is located at the distal tip of the catheter assembly (not shown) and sensor 22B is a reference transducer located elsewhere. Each of the sensors contains an optically resonant structure 21A and 21B consisting of two parallel reflecting surfaces 27A, 29A and 27B, 29B separated by a hollow cavity 26A and 26B to form a Fabry-Perot gap. The cavities of sensors 22A and 22B are maintained at a vacuum, while a pressure to be measured is applied to the pressure sensitive surface 25A of sensor 22A.

The reflected light beams from sensors 22A and 22B are transmitted via fiber optics 16A and 16B and beamsplitters 104, 106, 108, 110 and 112 to separate photodetectors 30A and 30B as described above. Each photodetector comprises means 52A and 52B and 60A and 60B for integrating the intensity of the reflected light beam directed thereto over a first and a second different wavelength bands. Preferably, means 52A and 60A are a first pair of short pass and long pass optical filters centered on a preselected wavelength from the first wavelength band of beam 114 from light source 48, and means 52B and 60B are a second pair of optical filters centered on a different preselected wavelength selected from the second wavelength band of beam 116.

The integrated signals are sent via connector means 94A, 96A,94B,96B to means 90A and 90B respectively for taking the ratio of the two integrated signals to produce from each reflected light beam a normalized signal output at connectors 92A and 92B. The normalized signals are independent of the absolute intensity of the reflected light beam. (For example photodetector 30A takes the ratio of the integrated signals from short pass and long pass filters 52A and 60A.) The resulting signal from each photodetector represents a measure only of the distance between the reflecting surfaces of the sensor from which it emanates. The normalized signals output at terminals 92A and 92B are then transmitted via connectors 93A and 93B to means 147 for subtracting the signal transmitted via connector 93A from the signal transmitted via connector 93B to yield a signal representing the difference between the applied pressure and the reference pressure output at terminal 118.

It is especially preferred that photodetectors 52A 60A,52B, 60B, divider means 90A,90B and means 117 for subtracting the signals output from the divider means be such that when the input voltage received at input terminal 120 is the same as the output voltage provided by any of the common types of hospital monitor devices, which can be either direct, alternating, or pulsed, the said photodetector assembly "scales" the input voltage by the above described operations thereon to generate an electrical signal at output terminal 118 that can be returned to the monitor for display as a pressure measurement reading. In other words, the preferred photodetector assembly produces an output signal that "looks" like one produced by a Wheatstone bridge piezoresistive electrical pressure sensor.

When the pressure applied to reference sensor 22B is atmospheric and sensor 22A is vented to atmospheric pressure via conduit 41 and first lumen 70, the resultant measurement signal represents the gauge pressure at surface 25A of sensor 22A.

Any commercial photodetector device capable of performing the above operations can be used as photodetectors 30A and 30B, for example, the Model 1400 Multisensor System manufactured by Metricor Corporation (Woodenville, Wash.).

This technique of spectroscopic normalization is sensitive only to variations in the source light beam, with spectral microshifts appearing as pressure changes for an individual sensor. By using the same light source for both sensors and computing the difference as described above to find the pressure, any microshifts in the spectrum that might occur in the source beam during the course of the monitoring period will affect both reflected beams equally and thus cancel at the ratio taking step.

As has been mentioned, the catheter assembly employing a multiwavelength light source 48 is self-correcting for changes in the intensity of light source 48 and changes in light transmission intensity due to bending of optical fibers and due to light loss in optical connectors. Both short and long wavelength output light band from optical filters 52 and 160 (FIG. 7) and 52A, 52B, 60A, and 60B (FIG. 8) are effected equally by intensity changes. Accordingly, when their respective amplified first and second electrical signals are divided in divider circuit 168 (FIG. 7) or divider means 90A and 90B (FIG. 8), such changes cancel each other out and have no effect on the output measuring light signal therefrom. Such dividing of two signals is known as ratiometric signal processing.

Moreover, to self correct for signal errors resulting from temperature effects upon the LED's, optical filters 52, 160, 52A, 52B, 60A and 60B are selected such that temperature changes produce a microshift in their respective output light band equal to and in the same direction as is produced by temperature in the LED. Similarly, beamsplitters 108 and 112 optionally can contain filters selected to accomplish the same goal with regard to source 48, when it is an LED. Therefore, the microshift in the operating signal produced by temperature effect in the LED is cancelled by the corresponding microshift produced in the operating segment by selection of the filter. Thus, photodetector assembly means 50 and 100 are self-correcting for any microshift in output signal caused by effects other than those caused by changes in the measured pressure.

It is within the scope of the present invention to eliminate the inaccuracies in the output measuring signal discussed above by having photodetector assembly means 100 take the ratio of the electrical signals corresponding to any two different portions of the output light from the sensors, even wherein one portion may be the entire output light from the sensor.

Light source 48 can comprise at least two sources of monochromatic light such as lasers or laser diodes, if a minimum of two wavelengths are required. Alternatively, it could comprise one or more sources of a plurality of wavelengths, such as LED's or white light sources, along with suitable optical filters, as needed, to provide at least two input measuring light wavelengths and/or wavelength bands.

However, it is preferred for simplicity that light source 48 be a single LED whose band width is substantially less than the resonant cycle length of the reflectivity curve of optically resonant structure 21.

The theoretical constraints on operation of the ratiometric preferred embodiments of the spectral modulation sensor require different operational parameters to avoid ambiguity in the output signal than are required with monochromatic light. The ratiometric embodiments, it will be remembered, require at least two different input measuring light wavelengths to the photodetector assembly.

It is known that when multiwavelength source light is used, the output light signal from spectral modulation sensor 22 contains a minimum of ambiguity when the maximum length and the maximum microshifting of the operating segment on its reflectivity curve both approach but do not exceed about one full resonance cycle. This criteria is different than that for the embodiment of the invention employing monochromatic input measuring light. In that case the maximum length and maximum microshifting of the operating segment of the reflectivity curve should not exceed one-half of a resonance cycle. Of course, the length and microshifting of the operating segment may be selected to be considerably less than the maximum allowable so as to improve linearity in the output light signal of optical resonance structure 21.

Figure 9:
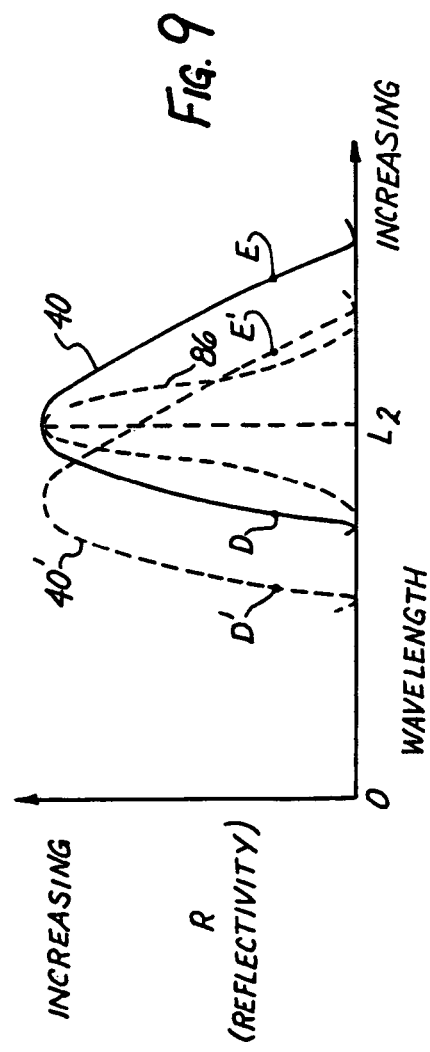
FIG. 9 is a graphic representation of the spectrally modulated output light from a spectral modulation sensor having multiwavelength input light.

The intensity curve of the output light of multiwavelength light source 48 is shown in FIG. 9 by curve 86, wherein light source 48 is a single LED. Wavelength $L_2$ is, by way of example, selected to be at or near the most intense output wavelength of light from said light source. Also schematically shown in FIG. 9 is an enlarged portion of reflectivity curve 40 taken from FIG. 5, which illustrates by way of example, operating segment DE on reflectivity curve 40 on optically resonant structure 21 and corresponding reflectivity curve 40' and operating segments D'E' which result from a shift of reflectivity curve 40 to the left due to the influence of sensed pressure on the distance between the reflective surfaces of optically resonant structure 21. Reflectivity curve 40 and its operating segment DE could also be shifted to the right in the same manner, but this is not illustrated in FIG. 9 for clarity.

The optically resonant structures used in this preferred embodiment of the invention and described in U.S. Pat. No. 4,678,904 are fabricated from a silicon wafer using photolithography and micromachining processes. These sensors are remarkably free from the phenomenon commonly known as "drift" wherein the "zero" reading of the transducer varies over time. When the spectral modulation sensors are employed in an intracranial pressure monitoring assembly the reliability and constancy of the pressure reading is of utmost importance. Dangerously elevated pressures in the brain are usually on the order of only about 50 mm Hg so that small inaccuracies in pressure readings may have dangerous consequences.

However, all pressure sensors are subject in some degree to inaccuracies wherein the monitor reads some pressure other than zero in the absence of any applied pressure and to calibration error, wherein the transducer reading is larger or smaller over the range of measured pressure than it should be. But an intracranial catheter cannot be removed to check the accuracy of the reading without subjecting the patient to increased risks of trauma and infection.

Therefore, in one embodiment of the invention, the pressure monitoring assembly is designed to allow correction of the offset error and any calibration error without removing the applied pressure and venting the transducer to atmospheric pressure (ie. without removing the catheter from the patient's brain). The problem is eliminated by providing a means for positioning the pressure sensitive diaphragm of the sensor in the same position as it would occupy under the condition of equal pressures so as to allow for in situ calibration testing.

Figure 10:
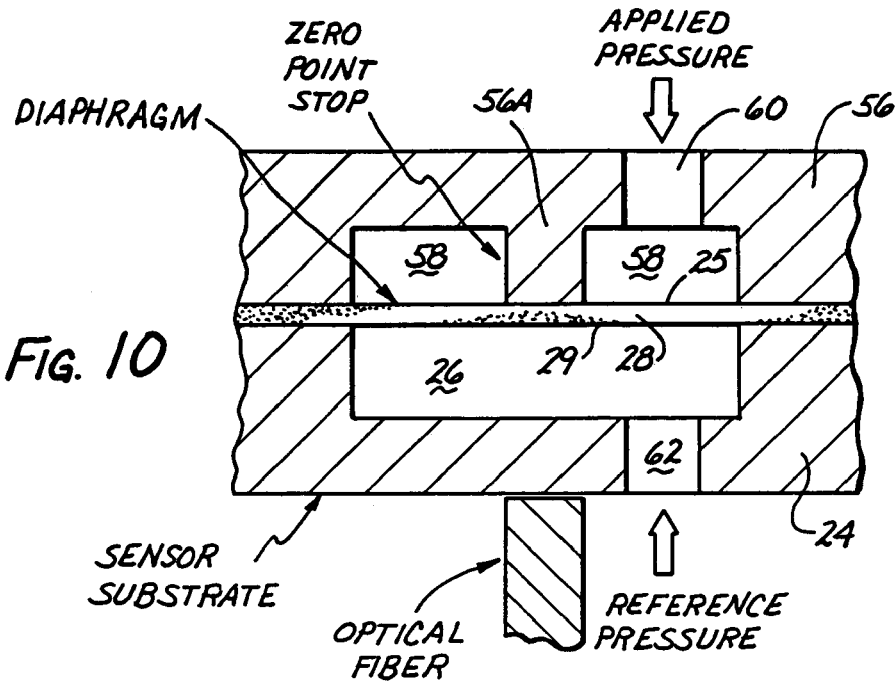
FIG. 10 is a cross-sectional view of a spectral modulation sensor having a zero stop.

As is shown in FIG. 10, to provide for in situ calibration of the sensor, during fabrication of circular pressure sensitive diaphragm 28, a ground and polished glass wafer 56, between about 0.005 and 0.025 inch thick, preferably about 0.011 inch thick, is bonded concentrically thereto. Glass wafer 56 is chemically etched using known methods to form a circular channel 58 concentric to the center point of the wafer, the width of the channel usually being between about 0.002 and 0.010 inch. Etching of the channel leaves an outer concentric raised ring and an inner raised concentrically circular plateau, or "stop" 56A on the surface of the glass wafer. Glass wafer 56 and substrate 24 are chemically bonded concentrically to surface 25 of circular diaphragm 28 such that the centers of the circular substrate, diaphragm, and glass wafer are coaxially aligned. When so aligned, the surface of "stop" 56A formed by etching the channel into the glass wafer rests against surface 25 of diaphragm 28, but is not bonded thereto. The outer radius of channel 58 has a diameter equal to or greater than that of circular cavity 26 etched into substrate 24.

Figure 11:
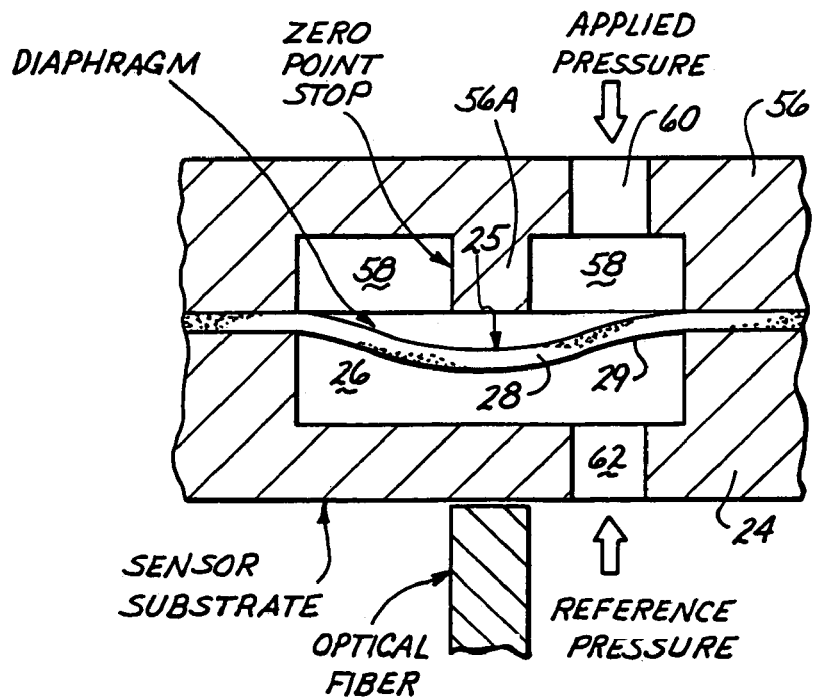
FIG. 11 is an illustration of the sensor of FIG. 10 under applied pressure.

Thus, as is shown in FIG. 10, under zero pressure surface 25 of diaphragm 28 is flush against the surface of the stop 56A. But, as is shown in FIG. 11, under applied pressure surface 25 of diaphragm 28 is deflected from the stop a distance proportional to or at least functionally related to the amount of applied pressure.

Wafer 56 contains aperture 60 therethrough opening into channel 58, through which aperture an applied pressure impinges upon and deflects diaphragm 28. Substrate 24 contains aperture 62, in fluid communication with the first lumen, which houses the sensor, aperture 62 preferably having a cross-sectional area equal to that of aperture 60, whereby a selected reference pressure, such as atmospheric pressure, impinges upon surface 29 of diaphragm 28 so as to exert a force opposite to that of the applied pressure. When the reference pressure exerted against surface 29 is equal to or greater than that of the applied pressure, as shown in FIG. 10, surface 25 of diaphragm 28 is restored to zero pressure position and rests flush against stop 56A.

An in vivo calibration reading indicating the offset error contained in the reading on the monitor can be obtained by slowly increasing the amount of back pressure applied to surface 29 of diaphragm 28 via vent 62 and the first lumen until the reading on the monitor ceases to fall and attains a constant low value. This constant low value represents the zero error of the system and should be subtracted from all pressure readings in obtaining a true pressure reading. In addition, the calibration accuracy of the transducer system can be obtained without the need to remove it from its location of operation if a manometer or other means of applying a known back pressure is used to measure the amount of pressure applied through aperture 62 against surface 29. The difference between the known back pressure and the constant pressure reading on the monitor generated when the diaphragm is restored to its zero position can be used to obtain the calibration error of the system.

Alternatively, the calibration error can be found by applying a known vacuum to surface 29 of diaphragm 25, which technique is equivalent to applying a positive pressure to the opposite side of the diaphragm. The displacement caused by the vacuum will result in a pressure being displayed on the monitor that can be evaluated using known methods against the known negative pressure to determine the calibration error. Once known, the operator can use the zero error and the calibration error to obtain the true pressure reading at any time without withdrawing the catheter from its location of operation.

The ability to calibrate and zero the instrument in situ offers a great advantage for any application requiring uninterrupted monitoring of the variable of interest, such as the pressure of a fluid stream in a chemical plant, and the like. This ability also has important clinical significance for monitoring intracranial pressure because the intracranial pressure catheter can be left in place for up to about five days according to current clinical practice while periodic checks are made to determine the integrity and accuracy of the system.

As shown in FIGS. 10 and 11, aperture 62 and the first lumen can also be used to vent the system to atmospheric pressure to obtain a gauge pressure measurement without contaminating the fluid system because diaphragm 28 serves as a protective barrier between the atmosphere and the fluid system under observation. Atmospheric gauge pressure readings are commonly preferred for monitoring pressure of bodily fluids, such as blood pressure, since the body is at atmospheric pressure. When the fluid system is the bloodstream or the intracranial cavity, and the like, this safety feature is highly desirable. It is also of great importance when monitoring any fluid stream that might be compromised by contact with the constituents of air.

A less preferred type of fiber optic pressure sensor adapted for use in the present invention is described in European patent 0127476, which is hereby incorporated by reference in its entirety, and is schematically illustrated in FIG. 12. The apparatus includes catheter housing 111 comprised of a first lumen 116 having a first set of optical fibers and a second fluid transport lumen 129. The first set of fibers includes emitter fiber 115 and return fiber 117 for transmitting a first light beam to and from the remote end of the catheter. In this type of pressure transducer, the removable reflective surface is mounted on bellows 119 located at the distal end of the catheter. Reflective surface 121 moves in accordance with pressure and thereby modulates the intensity of the first light beam, not by microshifts in the operating segment of the reflectivity curve of an optically resonant structure, but by scattering of the source light beam caused by movement of the reflective bellows, as is described in detail in European patent application 0127476. This type of optical sensor can be used with monochromatic light or with the multiwavelength light produced by LED 123 and transmitted by the first set of optical fibers to a first photodetector means 125, for detecting the modulated intensity of the reflected beam caused by movement of bellows 119.

Since bending of the catheter 111 effects the light transmittance of both the emitter fiber 115 and return fiber 117, the pressure monitoring apparatus optionally includes a reference channel comprised of a second set of optical fibers located within first lumen 116 and extending substantially along its entire length. This reference channel is used to determine the effects of bending on transmittance and to determine the effects of temperature and aging on the efficiency of LED 123 and photodetector 125. Since the first and second set of optical fibers are substantially coextensive and experience substantially the same degree of bending within catheter 111, the effect of that bending on their respective transmittances is presumed to be substantially equivalent.

A second light beam produced by LED 123 is transmitted by the second set of optical fibers so that variation in transmittance of the fibers and variations in light from the LED can be determined and a corresponding correction made to the intensity signal. The second set of optical fibers includes an emitter fiber 137 for transmitting the second light beam from LED 123 to a location near the distal end of catheter 111 and a return fiber 139 for transmitting the light beam back from that location. A second photodetector means 141 detects the intensity of this reflected light beam, and produces a correction signal on line 143 having an electrical current whose magnitude is proportional to intensity. Preferably, the correction signal is sent to control means 145 for generating a feedback control signal to be sent to light source 123 via power box 145 to compensate for any variation in light intensity caused by transmission losses such as those resulting from bending of the optical fibers and thereby to correct the measurement signal issuing from photodetector 125 at output terminal 146.

To standardize the intensity of the reflectivity of the reference sensor, a translucent droplet 145 of an epoxy containing a white pigment bonds together the remote ends of the second set of fibers and thereby reflects a predetermined fixed proportion of a light beam from the emitter fiber to the return fiber. The epoxy droplet is preferably coated with an opaque silver paint, the opacity preventing movement of adjacent reflective bellows 119 from effecting the reflected beam and the silver color maximizing the intensity of the reflected beam.

The above described photodetector assembly can be fashioned by one skilled in the art from commercially available elements. A type of photodetector apparatus suitable for use in this invention is Model OLM manufactured by Camino Laboratories, which interfaces with standard patient monitors.

This type of intensity modulation sensor requires that the first lumen be large enough to enclose at least two optical fibers, and four optical fibers are required if the reference channel is used. Therefore, the catheter housing is larger than that required for the spectral modulation sensor, which preferably uses a single optical fiber. For this reason, spectral modulation sensors are favored for use in intracranial pressure monitoring catheters.

From the foregoing various further applications, modifications, and adaptations of the invention within the scope of the claims appended hereto will be apparent to those skilled in the art to which it pertains. All embodiments, examples and alternatives, and the like, set forth herein are strictly intended as non-limiting examples.

We claim:

1. An intracranial pressure monitoring catheter device which is insertable into the cranium of a mammal through a bore hole of the cranium comprising:
   an elongate, tubular flexible catheter body having a proximal end, a distal end, and an outer sidewall;
   a pressure transmitting component for receiving the pressure at the distal end of said catheter body and for transmitting an indication of said pressure through said catheter body to the proximal end thereof;
   a connector on the proximal end of said catheter body for connecting said pressure transmitting component to an extracorporeal pressure monitoring device;
   a stylet insertion aperture formed in the side wall of the catheter body near the distal end of the catheter body, a distal portion of the catheter body being thus defined between the stylet insertion aperture and the catheter body distal end; and
   a stylet lumen extending between the stylet insertion aperture and the distal end of the catheter body, the stylet lumen being closed at the distal end of the catheter body;
   said catheter device being thereby configured such that a rigid stylet may be inserted through said stylet insertion aperture and advanced in the distal direction through said stylet receiving lumen to the closed distal end thereof to impart stiffness to only the distal portion of the catheter body, the catheter device being adapted to be fed through a scalp tunnel formed between two scalp incisions, one of the scalp incisions being coincident with the bore hole in the cranium, the catheter body being sized so that it may extend through the scalp tunnel with the proximal and distal ends of the catheter body extending out of respective ones of said scalp incisions, the distal portion being sized so that it can be pulled up and away from the bore hole and the stylet inserted into the stylet insertion aperture to impart stiffness to the distal portion and thereby facilitate insertion through the bore hole;
   wherein said stylet insertion aperture is formed in said sidewall at a location approximately four (4) inches from the distal end of said catheter body.

2. An intracranial pressure monitoring catheter device which is insertable into the cranium of a mammal through a bore hole of the cranium comprising:
   an elongate, tubular flexible catheter body having a proximal end, a distal end, and an outer sidewall;
   a pressure transmitting component for receiving the pressure at the distal end of said catheter body and for transmitting an indication of said pressure through said catheter body to the proximal end thereof;
   a connector on the proximal end of said catheter body for connecting said pressure transmitting component to an extracorporeal pressure monitoring device;
   a stylet insertion aperture formed in the side wall of the catheter body near the distal end of the catheter body, a distal portion of the catheter body being thus defined between the stylet insertion aperture and the catheter body distal end; and
   a stylet lumen extending between the stylet insertion aperture and the distal end of the catheter body, the stylet lumen being closed at the distal end of the catheter body;
   said catheter device being thereby configured such that a rigid stylet may be inserted through said stylet insertion aperture and advanced in the distal direction through said stylet receiving lumen to the closed distal end thereof to impart stiffness to only the distal portion of the catheter body, the catheter device being adapted to be fed through a scalp tunnel formed between two scalp incisions, one of the scalp incisions being coincident with the bore hole in the cranium, the catheter body being sized so that it may extend through the scalp tunnel with the proximal and distal ends of the catheter body extending out of respective ones of said scalp incisions, the distal portion being sized so that it can be pulled uP and away from the bore hole and the stylet inserted into the stylet insertion aperture to impart stiffness to the distal portion and thereby facilitate insertion through the bore hole;
   wherein said stylet insertion aperture is formed in said sidewall at a location approximately 15 cm from the distal end of said catheter body.

3. An intracranial pressure monitoring catheter device which is insertable into the cranium of a mammal through a bore hole of the cranium comprising:
   an elongate, tubular flexible catheter body having a proximal end, a distal end, and an outer sidewall;
   a pressure transmitting component for receiving the pressure at the distal end of said catheter body and for transmitting an indication of said pressure through said catheter body to the proximal end thereof;
   a connector on the proximal end of said catheter body for connecting said pressure transmitting component to an extracorporeal pressure monitoring device;
   a stylet insertion aperture formed in the side wall of the catheter body near the distal end of the catheter body, a distal portion of the catheter body being thus defined between the stylet insertion aperture and the catheter body distal end; and
   a stylet lumen extending between the stylet insertion aperture and the distal end of the catheter body, the stylet lumen being closed at the distal end of the catheter body;
   said catheter device being thereby configured such that a rigid stylet may be inserted through said stylet insertion aperture and advanced in the distal direction through said stylet receiving lumen to the closed distal end thereof to impart stiffness to only the distal portion of the catheter body, the catheter device being adapted to be fed through a scalp tunnel formed between two scalp incisions, one of the scalp incisions being coincident with the bore hole in the cranium, the catheter body being sized so that it may extend through the scalp tunnel with the proximal and distal ends of the catheter body extending out of respective ones of said scalp incisions, the distal portion being sized so that it can be pulled uP and away from the bore hole and the stylet inserted into the stylet insertion aperture to impart stiffness to the distal portion and thereby facilitate insertion through the bore hole;
   wherein said connector for connecting said pressure transmitting component to said extracorporeal pressure monitoring device comprises a connector body which is larger in cross-sectional dimension than said catheter body.

4. A pressure monitoring catheter system comprising the combination of:
   a) an intracranial pressure monitoring catheter device which is insertable into the cranium of a mammal through a bore hole of the cranium comprising:
      an elongate, tubular flexible catheter body having a proximal end, a distal end, and an outer sidewall;
      a pressure transmitting component for receiving the pressure at the distal end of said catheter body and for transmitting an indication of said pressure through said catheter body to the proximal end thereof;

a connector on the proximal end of said catheter body for connecting said pressure transmitting component to an extracorporeal pressure monitoring device;

a stylet insertion aperture formed in the side wall of the catheter body near the distal end of the catheter body, a distal portion of the catheter body being thus defined between the stylet insertion aperture and the catheter body distal end; and a stylet lumen extending between the stylet insertion aperture and the distal end of the catheter body, the stylet lumen being closed at the distal end of the catheter body;

said catheter device being thereby configured such that a rigid stylet may be inserted through said stylet insertion aperture and advanced in the distal direction through said stylet receiving lumen to the closed distal end thereof to impart stiffness to only the distal portion of the catheter body, the catheter device being adapted to be fed through a scalp tunnel formed between two scalp incisions, one of the scalp incisions being coincident with the bore hole in the cranium, the catheter body being sized so that it may extend through the scalp tunnel with the proximal and distal ends of the catheter body extending out of respective ones of said scalp incisions, the distal portion being sized so that it can be pulled up and away from the bore hole and the stylet inserted into the stylet insertion aperture to impart stiffness to the distal portion and thereby facilitate insertion through the bore hole; and b) an elongate rigid stylet having a proximal end and a distal end, said stylet being shorter than said catheter body and insertable into said stylet lumen for the purpose of imparting stiffness only to said distal portion of said catheter body.

5. An intracranial pressure monitoring catheter system wherein a catheter is passable through a subcutaneous scalp tunnel which extends between a first scalp incision and a second scalp incision, and wherein said catheter is subsequently insertable into the cranium through a bore hole formed in the cranium beneath said second scalp incision, said system comprising:

a. a pressure monitoring catheter device comprising:

an elongate tubular flexible catheter body having a proximal end, a distal end and an outer surface;

a pressure transmitting component for receiving the pressure at the distal end of said catheter body and for transmitting an indication of the pressure at the distal end of said catheter body to the proximal end of said catheter body;

a connector on the proximal end of said catheter body for connecting said pressure transmitting component to an extracorporeal pressure monitoring device;

a stylet insertion aperture formed in the side wall of the catheter body near the distal end of the catheter body, a distal portion of the catheter body being thus defined between the stylet insertion aperture and the catheter body distal end; and a stylet lumen extending between the stylet insertion aperture and the distal end of the catheter body, the stylet lumen being closed at the distal end of the catheter body; and b. a stylet which is shorter than said catheter body, said stylet being insertable into, and removable from, said stylet lumen to impart stiffness to only said distal portion of said catheter body;

c. said intracranial pressure monitoring catheter system being thereby constructed and configured for insertion into the cranium by:

i) initially inserting the distal end of said catheter body into said subcutaneous scalp tunnel through said first scalp incision;

ii) advancing a portion of said catheter body through said subcutaneous scalp tunnel and out of said second scalp incision such that said stylet insertion aperture and said distal portion of the catheter body are exteriorized out of said second scalp incision;

iii) inserting said stylet through said stylet insertion aperture and into said stylet lumen;

iv) introducing the distal end of said catheter body through said bore hole and advancing said distal portion of said catheter body into said cranium such that said stylet insertion aperture remains outside of said cranium;

v) removing said stylet from said catheter body; and, vi) effecting closure of said second scalp incision over said catheter body.

6. The pressure monitoring catheter system of claim 5 wherein:

said stylet insertion aperture is located approximately four (4) inches from the distal end of said catheter body.

7. The pressure monitoring catheter system of claim 5 wherein:

said stylet insertion aperture is located approximately 15 cm from the distal end of said catheter body.

8. The pressure monitoring catheter system of claim 5 wherein said pressure transmitting component comprises an optical pressure sensing system.

9. The pressure monitoring catheter system of claim 8 wherein said optical pressure sensing system comprises:

a light-reflective diaphragm positioned at the distal end of said catheter body, said diaphragm being constructed and positioned so as to move in accordance with changes in pressure at the distal end of said catheter;

a distally directed light transmitting member extending longitudinally through said catheter body, said distally directed light transmitting member having a proximal end and a distal end, the proximal end of said distally directed light transmitting member being connectable to a light source such that light from said light source will be transmitted in the distal direction, through said distally directed light transmitting member, to said light-reflective diaphragm positioned at the distal end of said catheter;

a proximally directed light transmitting member extending longitudinally through said catheter, said proximally directed light transmitting member having a proximal end and a distal end, said proximally directed light transmitting member being configured and positioned to transmit reflected light from said light-reflecting diaphragm, in the proximal direction, to the proximal end of said catheter; and the proximal end of said proximally directed light transmitting member being connectable by way of said connector to a monitoring device operative to generate indicia of pressure relative to changes in said reflected light received from said proximally directed light transmitting member.

10. The pressure monitoring catheter system of claim 6 further comprising at least one drainage lumen for draining intracranial cerebrospinal fluid, said at least one fluid drainage lumen being formed separate and apart form said stylet lumen, said at least one fluid drainage lumen comprising:

a hollow passageway extending longitudinally through said catheter body;

at least one distal drainage aperture to permit cerebrospinal fluid to enter said at least one fluid drainage lumen; and a proximal outlet aperture to permit cerebrospinal fluid to exit said at least one distal drainage lumen.

11. The pressure monitoring catheter system of claim 10 wherein said at least one distal drainage aperture comprises:

a plurality of apertures aligned in a longitudinal row near the distal end of said catheter body and forming openings into said drainage lumen.

12. The pressure monitoring catheter system of claim 10 wherein said at least one distal drainage aperture comprises:

a plurality of longitudinal rows of apertures formed near the distal end of said catheter body and opening into said at least one fluid drainage lumen.

13. The pressure monitoring catheter system of claim 5 wherein said connector for connecting said pressure transmitting component to said pressure monitoring device comprises a connector body which is larger in cross-sectional dimension than said catheter body.

14. The pressure monitoring catheter system of claim 5 wherein said connector for connecting said pressure transmitting component to said pressure monitoring device comprises a fiber optic connector.

* * * * *